(12) United States Patent
Patangay et al.

(10) Patent No.: US 7,853,327 B2
(45) Date of Patent: Dec. 14, 2010

(54) HEART SOUND TRACKING SYSTEM AND METHOD

(75) Inventors: Abhilash Patangay, Little Canada, MN (US); Krzysztof Z. Siejko, Maple Grove, MN (US); Gerrard M. Carlson, Champlin, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 854 days.

(21) Appl. No.: 11/736,055

(22) Filed: Apr. 17, 2007

(65) Prior Publication Data

US 2008/0262368 A1    Oct. 23, 2008

(51) Int. Cl.
*A61N 1/365* (2006.01)
(52) U.S. Cl. .......................................... 607/17; 600/513
(58) Field of Classification Search ................... 607/17; 600/513
See application file for complete search history.

(56) References Cited

U.S. PATENT DOCUMENTS

| | | | |
|---|---|---|---|
| 4,220,160 A | 9/1980 | Kimball et al. |
| 4,967,760 A | 11/1990 | Bennett et al. |
| 5,012,815 A | 5/1991 | Bennett, Jr. et al. |
| 5,025,809 A | 6/1991 | Johnson et al. |
| 5,305,745 A | 4/1994 | Zacouto |
| 5,630,835 A | 5/1997 | Brownlee |
| 5,687,738 A | 11/1997 | Shapiro et al. |
| 5,792,195 A | 8/1998 | Carlson et al. |
| 5,957,866 A | 9/1999 | Shapiro et al. |
| 6,243,606 B1 | 6/2001 | Mann et al. |
| 6,440,082 B1 | 8/2002 | Joo et al. |
| 6,527,729 B1 | 3/2003 | Turcott |
| 6,629,937 B2 | 10/2003 | Watrous |

(Continued)

FOREIGN PATENT DOCUMENTS

WO   WO-2004/035137 A1   4/2004

(Continued)

OTHER PUBLICATIONS

"U.S. Appl. No. 10/746,853, Amendment and Response filed Jan. 17, 2008 to Non-Final Office Action mailed Sep. 26, 2007", 18 pgs.

(Continued)

*Primary Examiner*—Carl H. Layno
*Assistant Examiner*—Jon-Eric C. Morales
(74) *Attorney, Agent, or Firm*—Schwegman, Lundberg & Woessner, P.A.

(57) ABSTRACT

A system and method provide heart sound tracking, including an input circuit, configured to receive heart sound information, and a heart sound recognition circuit. The heart sound recognition circuit can be coupled to the input circuit and can be configured to recognize, within a particular heart sound of a particular heart sound waveform, a first intra heart sound energy indication and a corresponding first intra heart sound time indication using the heart sound information from the particular heart sound waveform and the heart sound information from at least one other heart sound waveform. The particular heart sound can include at least a portion of one of S1, S2, S3, and S4. Further, the first intra heart sound energy indication and the corresponding first intra heart sound time indication can correspond to the at least a portion of one of S1, S2, S3, and S4, respectively.

35 Claims, 8 Drawing Sheets

U.S. PATENT DOCUMENTS

| | | |
|---|---|---|
| 6,643,548 B1 | 11/2003 | Mai et al. |
| 6,643,584 B1 | 11/2003 | Ikeuchi et al. |
| 6,650,940 B1 | 11/2003 | Zhu et al. |
| 6,824,519 B2 | 11/2004 | Narimatsu et al. |
| 6,845,263 B2 | 1/2005 | Kawaguchi |
| 6,868,346 B2 | 3/2005 | Larson et al. |
| 6,999,816 B2 | 2/2006 | Van |
| 7,052,466 B2 | 5/2006 | Scheiner et al. |
| 7,096,060 B2 | 8/2006 | Arand et al. |
| 7,115,096 B2 | 10/2006 | Siejko et al. |
| 7,123,962 B2 | 10/2006 | Siejko et al. |
| 7,174,203 B2 | 2/2007 | Arand et al. |
| 7,431,699 B2 | 10/2008 | Siejko et al. |
| 2002/0001390 A1 | 1/2002 | Kawaguchi |
| 2002/0035337 A1 | 3/2002 | Oka |
| 2002/0107450 A1 | 8/2002 | Ogura |
| 2002/0151812 A1 | 10/2002 | Scheiner et al. |
| 2002/0151938 A1 | 10/2002 | Corbucci |
| 2003/0055352 A1 | 3/2003 | Hayek et al. |
| 2003/0055461 A1 | 3/2003 | Girouard et al. |
| 2003/0093003 A1 | 5/2003 | Watrous et al. |
| 2003/0120159 A1 | 6/2003 | Mohler |
| 2003/0229289 A1 | 12/2003 | Mohler |
| 2004/0064056 A1 | 4/2004 | Ogura |
| 2004/0106960 A1 | 6/2004 | Siejko et al. |
| 2004/0106961 A1 | 6/2004 | Siejko et al. |
| 2004/0127792 A1 | 7/2004 | Siejko et al. |
| 2004/0138572 A1 | 7/2004 | Thiagarajan |
| 2004/0167417 A1 | 8/2004 | Schulhauser et al. |
| 2004/0215264 A1 | 10/2004 | Van Bentem |
| 2004/0236239 A1 | 11/2004 | Murray et al. |
| 2004/0267148 A1 | 12/2004 | Arand et al. |
| 2005/0102001 A1 | 5/2005 | Maile et al. |
| 2005/0107838 A1 | 5/2005 | Lovett et al. |
| 2005/0115561 A1 | 6/2005 | Stahmann et al. |
| 2005/0137626 A1 | 6/2005 | Pastore et al. |
| 2005/0148896 A1 | 7/2005 | Siejko et al. |
| 2005/0149136 A1 | 7/2005 | Siejko et al. |
| 2006/0020294 A1* | 1/2006 | Brockway et al. ............ 607/17 |
| 2006/0047213 A1* | 3/2006 | Gavriely et al. ............ 600/513 |
| 2006/0247550 A1 | 11/2006 | Thiagarajan et al. |
| 2006/0282000 A1 | 12/2006 | Zhang et al. |
| 2007/0078491 A1 | 4/2007 | Siejko et al. |
| 2007/0191725 A1 | 8/2007 | Nelson |
| 2008/0119749 A1 | 5/2008 | Haro et al. |
| 2008/0119750 A1 | 5/2008 | Patangay et al. |
| 2008/0125820 A1 | 5/2008 | Stahmann et al. |
| 2008/0177191 A1 | 7/2008 | Patangay et al. |
| 2009/0018461 A1 | 1/2009 | Siejko et al. |

FOREIGN PATENT DOCUMENTS

| | | |
|---|---|---|
| WO | WO-2008063288 A2 | 5/2008 |
| WO | WO-2008/130532 A1 | 10/2008 |

OTHER PUBLICATIONS

"U.S. Appl. No. 10/746,853, Notice of Allowance mailed May 30, 2008", 4 pgs.

"U.S. Appl. No. 10/746,853, Amendment and Response filed Mar. 15, 2007 to Non-Final Office Action mailed Dec. 19, 2006", 16 pgs.

"U.S. Appl. No. 10/746,853, Amendment and Response filed Jul. 23, 2007 to Final Office Action mailed May 22, 2007", 16 pgs.

"U.S. Appl. No. 10/746,853, Final Office Action mailed May 22, 2007", 11 pgs.

"U.S. Appl. No. 10/746,853, Non-Final Office Action mailed Sep. 26, 2007", 8 pgs.

"U.S. Appl. No. 10/746,853, Non-Final Office Action mailed Dec. 19, 2006", 10 pgs.

"U.S. Appl. No. 10/746,874, Notice of Allowance mailed May 19, 2006", 9 pgs.

"U.S. Appl. No. 10/746,874, Response filed Apr. 17, 2006 to Restriction Requirement mailed Mar. 31, 2006", 14 pgs.

"U.S. Appl. No. 10/746,874, Restriction Requirement mailed Mar. 31, 2006", 6 pgs.

"International Application Serial No. PCT/US2008/004832, International Search Report mailed Sep. 3, 2008", 3 pgs.

"International Application Serial No. PCT/US2008/004832, Written Opinion mailed Sep. 3, 2008", 7 pgs.

Bulgrin, J. R., et al., "Comparison of Short-Time Fourier, Wavelet and Time-Domain Analyses of Intracardiac Sounds", *Biomedical Sciences Instrumentation*, 29, (1993), 4 pgs.

Dreuw, P., et al., "Tracking Using Dynamic Programming for Appearance-Based Sign Language Recognition", *Proceedings of the 7th International Conference on Automatic Face and Gesture Recognition*, (2006),293-298.

Leatham, A., "Splitting of the First and Second Heart Sounds",*Lancet*, 267 (6839), (1954),607-614.

Marcus, G. M., et al., "Association Between Phonocardiographic Third and Fourth Heart Sounds and Objective Measures of Left Ventricular Function", *JAMA*, 293(18), (2005), 2238-2244.

Obaidat, M. S., et al., "Performance of the Short-Time Fourier Transform and Wavelet Transform to Phonocardiogram Signal Analysis", *Proceedings of the 1992 ACM/SIGAPP Symposium on Applied Computing ACM, Applied Computing: Technological Challenges of the 1990s*, (1992), 856-862.

"U.S. Appl. No. 10/924,402, U.S. Appl. No. 11/777,739, Restriction Requirement mailed Sep. 23, 2009 mailed Sep. 23, 2009", 7 pgs.

"U.S. Appl. No. 11/465,878, Notice of Allowance mailed Oct. 8, 2009", 8 pgs.

"U.S. Appl. No. 11/564,637 Restriction Requirement mailed Mar. 16, 2009", 6 pgs.

"U.S. Appl. No. 11/564,637, Non-Final Office Action mailed May 13, 2009", 7 pgs.

"U.S. Appl. No. 11/564,637, Response filed Apr. 16, 2009 to Restriction Requirement mailed Mar. 16, 2009", 6 pgs.

"U.S. Appl. No. 11/564,637, Response filed Aug. 13, 2009 to Non Final Office Action mailed May 13, 2009", 7 pgs.

"U.S. Appl. No. 11/561,428, Non-Final Office Action mailed Apr. 20, 2010", 13 pgs.

"U.S. Appl. No. 11/564,637, Examiner Interview Summary mailed Feb. 18, 2010", 5 pgs.

"U.S. Appl. No. 11/564,637, Final Office Action mailed Dec. 10, 2009", 9 pgs.

"U.S. Appl. No. 11/564,637, Response filed Feb. 23, 2010 to Final Office Action mailed Dec. 10, 2009", 9 pgs.

"U.S. Appl. No. 11/564,637, Response filed Feb. 23, 2010 to Final Office Action mailed Dec. 10, 2009", 9 pgs.

"U.S. Appl. No. 11/777,739, Response filed Apr. 29, 2010 to Non Final Office Action mailed Jan. 29, 2010", 18 pgs.

"U.S. Appl. No. 11/777,739, Final Office Action mailed Jun. 4, 2010", 16 pgs.

"U.S. Appl. No. 11/777,739, Non-Final Office Action mailed Jan. 29, 2010", 18 pgs.

"European Application No. 08742888.4, Office Action Mailed Feb. 12, 2010", 2 pgs.

* cited by examiner

HEART SOUND TRACKING SYSTEM AND METHOD

TECHNICAL FIELD

This patent document pertains generally to cardiac health, and more particularly, but not by way of limitation, to heart sounds tracking.

BACKGROUND

Heart sounds are generally associated with the mechanical vibrations from the activity of a subject's heart and the flow of blood through the heart. Because of this association, heart sounds typically recur with each cardiac cycle of a heart, and are typically separated and classified into one of four types according to the activity associated with the vibration: S1, S2, S3, and S4. S1 (commonly referred to in the art as "the first heart sound") is typically associated with the vibrational sound made by the heart during tensing of the mitral valve. S2 (commonly referred to in the art as "the second heart sound") is typically associated with the beginning of diastole. S3 (commonly referred to in the art as "the third heart sound") and S4 (commonly referred to in the art as "the fourth heart sound") are typically associated with the filling pressures of the left ventricle during diastole. Generally, heart sounds can be used as indications of proper or improper functioning of a subject's heart.

Overview

A heart sound is typically identified according to its amplitude and corresponding timing. In one example, a heart sound can be detected using a heart sound window established according to certain triggering events, such as certain components of an electrocardiogram ("ECG") signal. One method of identifying the heart sound includes detecting the maximum heart sound amplitude within the heart sound window. The heart sound, for that heart sound window, is then identified according to the value of the maximum heart sound amplitude and corresponding timing of the maximum amplitude. However, multiple peaks can be present within the heart sound signal of an individual heart sound. The present inventors have recognized, among other things, that the peak in the heart sound signal having the maximum amplitude may not be a desirable identifier of the heart sound.

This document discusses, among other things, a system and method for heart sound tracking, including an input circuit, configured to receive heart sound information, and a heart sound recognition circuit. The heart sound recognition circuit can be coupled to the input circuit and can be configured to recognize, within a particular heart sound of a particular heart sound waveform, a first intra heart sound energy indication and a corresponding first intra heart sound time indication using the heart sound information from the particular heart sound waveform and the heart sound information from at least one other heart sound waveform. The particular heart sound can include at least a portion of one of S1, S2, S3, and S4. Further, the first intra heart sound energy indication and the corresponding first intra heart sound time indication can correspond to the at least a portion of one of S1, S2, S3, and S4, respectively.

In Example 1, a system includes an input circuit, configured to receive heart sound information. The system also includes a heart sound recognition circuit, coupled to the input circuit, configured to recognize, within a particular heart sound of a particular heart sound waveform, a first intra heart sound energy indication and a corresponding first intra heart sound time indication using the heart sound information from the particular heart sound waveform and the heart sound information from at least one other heart sound waveform. In this example, the particular heart sound includes at least a portion of one of S1, S2, S3, and S4, and the first intra heart sound energy indication and the corresponding first intra heart sound time indication corresponds to the at least a portion of one of S1, S2, S3, and S4, respectively.

In Example 2, the input circuit of Example 1 is optionally configured to receive S2 information, and the heart sound recognition circuit is optionally configured to recognize, within the S2 of the particular heart sound waveform, an intra S2 energy indication and a corresponding intra S2 time indication using the S2 information from the particular heart sound waveform and the S2 information from at least one other heart sound waveform.

In Example 3, the heart sound waveform of Examples 1-2 optionally includes at least a portion of at least one physiological cycle.

In Example 4, the physiological cycle of Examples 1-3 optionally includes a cardiac cycle.

In Example 5, the particular heart sound of a particular heart sound waveform of Examples 1-4 optionally includes an ensemble averaged heart sound over multiple physiological cycles.

In Example 6, the at least one other heart sound waveform of Examples 1-5 optionally includes an immediately preceding heart sound waveform to the particular heart sound waveform.

In Example 7, the heart sound recognition circuit of Examples 1-6 is optionally configured to recognize the first intra heart sound energy indication and the corresponding first intra heart sound time indication using a heart sound template.

In Example 8, the heart sound template of Examples 1-7 optionally includes at least a portion of the heart sound information from the at least one other heart sound waveform.

In Example 9, the heart sound recognition circuit of Examples 1-8 is optionally configured to recognize the first intra heart sound energy indication and the corresponding first intra heart sound time indication using a cross correlation between at least a portion of the heart sound information from the particular heart sound waveform and at least a portion of the heart sound template.

In Example 10, the system of Examples 1-9 optionally includes an implantable medical device, including a heart sound sensor configured to sense a heart sound signal, and a heart sound feature detector, coupled to the heart sound sensor, the heart sound feature detector configured to detect at least one heart sound feature using the heart sound signal. In this example, the heart sound information of Examples 1-9 optionally includes the at least one heart sound feature.

In Example 11, the heart sound recognition circuit of Examples 1-10 optionally includes a detection circuit configured to: detect at least one first candidate heart sound for the particular heart sound of the at least one other heart sound waveform using the heart sound information, wherein the at least one first candidate heart sound includes an intra heart sound energy indication and a corresponding intra heart sound time indication; and detect at least one second candidate heart sound for the particular heart sound of the particular heart sound waveform using the heart sound information, wherein the at least one second candidate heart sound includes an intra heart sound energy indication and a corresponding intra heart sound time indication. In this example, the heart sound recognition circuit of Examples 1-10 is optionally configured to recognize the first intra heart sound energy indication and the corresponding first intra heart sound time indication using: the at least one detected first candidate heart sound; and the at least one detected second candidate heart sound.

In Example 12, the at least one other heart sound waveform of Examples 1-11 optionally includes an immediately preceding heart sound waveform to the particular heart sound waveform.

In Example 13, the heart sound recognition circuit of Examples 1-12 optionally includes a cost analysis circuit, coupled to the detection circuit, the cost analysis circuit configured to calculate a cost for the at least one second candidate heart sound, the calculated cost including: a jump penalty indicative of a temporal cost associated with the at least one second candidate heart sound; and a local score indicative of a local benefit associated with the at least one second candidate heart sound. In this example, the heart sound recognition circuit of Examples 1-12 is optionally configured to recognize the first intra heart sound energy indication and the corresponding first intra heart sound time indication using the calculated cost.

In Example 14, the heart sound recognition circuit of Examples 1-13 is optionally configured to calculate a back pointer that indicates a pointer from the at least one second candidate heart sound to an optimal at least one first candidate heart sound using the cost analysis.

In Example 15, the heart sound recognition circuit of Examples 1-14 optionally includes a coasting circuit, coupled to the heart sound recognition circuit, configured to disregard the recognized first intra heart sound energy indication and the corresponding recognized first intra heart sound time indication using a comparison of: the recognized first intra heart sound energy indication and the corresponding recognized first intra heart sound time indication; and at least one other recognized intra heart sound energy indication and a corresponding at least one other recognized intra heart sound time indication within the particular heart sound of at least one other heart sound waveform.

In Example 16, the heart sound recognition circuit of Examples 1-15 optionally includes a recapture circuit, coupled to the coasting circuit, configured recapture the disregarded recognized first intra heart sound energy indication and the corresponding disregarded recognized first intra heart sound time indication using a comparison of: the disregarded recognized first intra heart sound energy indication and the corresponding disregarded recognized first intra heart sound time indication; and at least one other recognized intra heart sound energy indication and a corresponding at least one other recognized intra heart sound time indication within the particular heart sound of at least one other heart sound waveform.

In Example 17, a system includes means for receiving heart sound information, such as by using an input circuit to receive heart sound information. The system also includes means for recognizing a first intra heart sound energy indication and a corresponding first intra heart sound time indication within a particular heart sound of a particular heart sound waveform using the heart sound information from the particular heart sound waveform and the heart sound information from at least one other heart sound waveform, such as by using a heart sound recognition circuit configured to recognize, within a particular heart sound of a particular heart sound waveform, a first intra heart sound energy indication and a corresponding first intra heart sound time indication using the heart sound information from the particular heart sound waveform and the heart sound information from at least one other heart sound waveform.

In Example 18, the system of Example 17 optionally includes means for disregarding the recognized first intra heart sound energy indication and the corresponding recognized first intra heart sound time indication, such as by using a coasting circuit configured to disregard the recognized first intra heart sound energy indication and the corresponding recognized first intra heart sound time indication using a comparison of: the recognized first intra heart sound energy indication and the corresponding recognized first intra heart sound time indication; and at least one other recognized intra heart sound energy indication and a corresponding at least one other recognized intra heart sound time indication within the particular heart sound of at least one other heart sound waveform.

In Example 19, the system of examples 17-18 optionally includes means for recapturing the disregarded recognized first intra heart sound energy indication and the corresponding disregarded recognized first intra heart sound time indication, such as by using a recapture circuit configured recapture the disregarded recognized first intra heart sound energy indication and the corresponding disregarded recognized first intra heart sound time indication using a comparison of: the disregarded recognized first intra heart sound energy indication and the corresponding disregarded recognized first intra heart sound time indication; and at least one other recognized intra heart sound energy indication and a corresponding at least one other recognized intra heart sound time indication within the particular heart sound of at least one other heart sound waveform.

In Example 20, a method includes receiving heart sound information. The method also includes recognizing a first intra heart sound energy indication and a corresponding first intra heart sound time indication within a particular heart sound of a particular heart sound waveform using the heart sound information from the particular heart sound waveform and the heart sound information from at least one other heart sound waveform. In this example, the recognizing the first intra heart sound energy indication and the corresponding first intra heart sound time indication within the particular heart sound includes recognizing within at least a portion of one of S1, S2, S3, and S4, and the recognizing the first intra heart sound energy indication and the corresponding first intra heart sound time indication corresponds to the at least a portion of one of S1, S2, S3, and S4, respectively.

In Example 21, the receiving the heart sound information of Example 20 optionally includes receiving S2 information, and the recognizing the first intra heart sound energy indication and the corresponding first intra heart sound time indication within the particular heart sound of the particular heart sound waveform of Example 20 optionally includes recognizing an intra S2 energy indication and a corresponding intra S2 time indication within an S2 of the particular heart sound waveform. In this example, the using the heart sound information from the particular heart sound waveform and the heart sound information from the at least one other heart sound waveform of Example 20 optionally includes using the S2 information from the particular heart sound waveform and the S2 information from at least one other heart sound waveform.

In Example 22, the heart sound waveform of Examples 20-21 optionally includes at least a portion of at least one physiological cycle.

In Example 23, the physiological cycle of Examples 20-22 optionally includes a cardiac cycle.

In Example 24, the particular heart sound of the particular heart sound waveform of Examples 20-23 optionally includes an ensemble averaged heart sound over multiple physiological cycles.

In Example 25, the using the heart sound information from the at least one other heart sound waveform of Examples 20-24 optionally includes using the heart sound information from an immediately preceding heart sound waveform to the particular heart sound waveform.

In Example 26, the recognizing the first intra heart sound energy indication and the corresponding first intra heart sound time indication of Examples 20-25 optionally includes using a heart sound template and comparing the heart sound information from the particular heart sound waveform to the heart sound template.

In Example 27, the using the heart sound template of Examples 20-26 optionally includes updating the heart sound template using at least a portion of the heart sound information from the at least one other heart sound waveform.

In Example 28, the recognizing the first intra heart sound energy indication and the corresponding first intra heart sound time indication of Examples 20-27 optionally includes cross correlating between at least a portion of the heart sound information from the particular heart sound waveform and at least a portion of the heart sound template.

In Example 29, the method of Examples 20-28 optionally includes implantably sensing a heart sound signal and implantably detecting at least one heart sound feature using the heart sound signal. In this example, the using the heart sound information of Examples 20-28 optionally includes using the at least one heart sound feature.

In Example 30, the method of Examples 20-29 optionally includes detecting at least one first candidate heart sound for the particular heart sound of the at least one other heart sound waveform using the heart sound information, wherein detecting the at least one first candidate heart sound includes detecting an intra heart sound energy indication and a corresponding intra heart sound time indication, and detecting at least one second candidate heart sound for the particular heart sound of the particular heart sound waveform using the heart sound information, wherein detecting the at least one second candidate heart sound includes detecting an intra heart sound energy indication and a corresponding intra heart sound time indication. In this example, the recognizing the first intra heart sound energy indication and the corresponding first intra heart sound time indication of Examples 20-29 optionally includes using: the at least one detected first candidate heart sound; and the at least one detected second candidate heart sound.

In Example 31, the recognizing the at least one first candidate heart sound for the particular heart sound of the at least one other heart sound waveform of Examples 20-30 optionally includes recognizing the at least one first candidate heart sound for the particular heart sound of an immediately preceding heart sound waveform to the particular heart sound waveform.

In Example 32, the method of Examples 20-31 optionally includes calculating a cost for the at least one second candidate heart sound, including: calculating a jump penalty indicative of a temporal cost associated with the at least one second candidate heart sound; and calculating a local score indicative of a local benefit associated with the at least one second candidate heart sound. In this example, the recognizing the first intra heart sound energy indication and the corresponding first intra heart sound time indication of Examples 20-31 optionally includes using the calculated cost.

In Example 33, the method of Examples 20-32 optionally includes calculating a back pointer that indicates a pointer from the at least one second candidate heart sound to an optimal at least one first candidate heart sound using the cost analysis.

In Example 34, the method of Examples 20-33 optionally includes disregarding the recognized first intra heart sound energy indication and the corresponding recognized first intra heart sound time indication using a comparison of: the recognized first intra heart sound energy indication and the corresponding recognized first intra heart sound time indication; and at least one other recognized intra heart sound energy indication and a corresponding at least one other recognized intra heart sound time indication within the particular heart sound of at least one other heart sound waveform.

In Example 35, the method of Examples 20-34 optionally includes recapturing the disregarded recognized first intra heart sound energy indication and the corresponding disregarded recognized first intra heart sound time indication using a comparison of: the disregarded recognized first intra heart sound energy indication and the corresponding disregarded recognized first intra heart sound time indication; and at least one other recognized intra heart sound energy indication and a corresponding at least one other recognized intra heart sound time indication within the particular heart sound of at least one other heart sound waveform.

This overview is intended to provide an overview of the subject matter of the present patent application. It is not intended to provide an exclusive or exhaustive explanation of the invention. The detailed description is included to provide further information about the subject matter of the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

Figure 1:
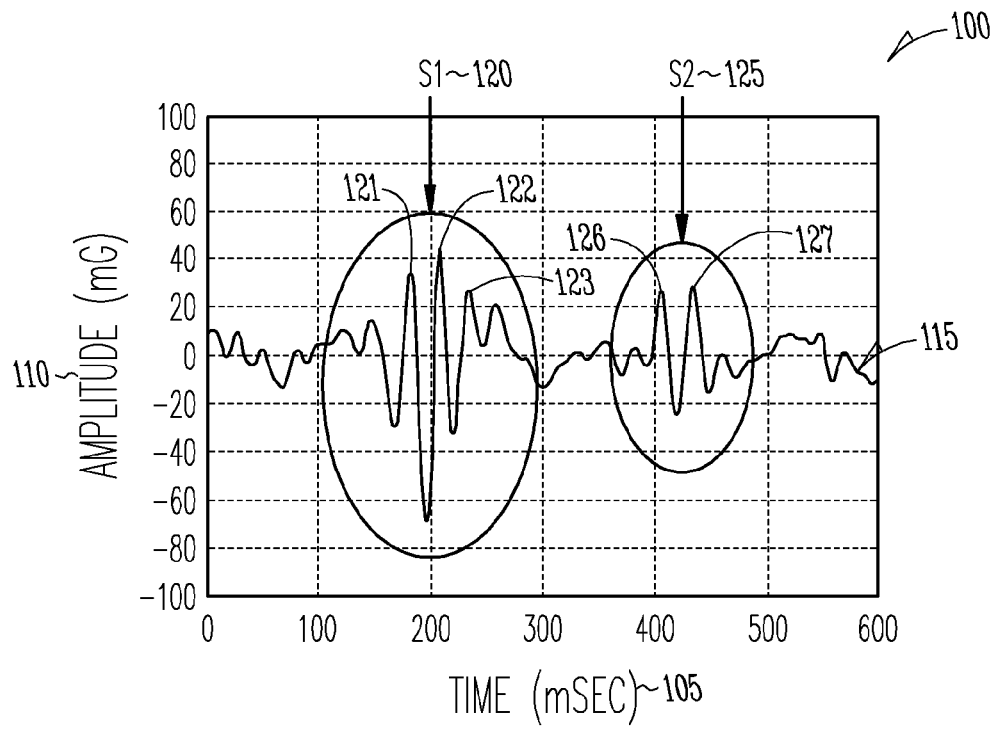
FIG. 1 illustrates generally an example of an illustration of portions of a heart sound signal including S1 and S2.

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, such that "A or B" includes "A but not B," "B but not A," and "A and B," unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Heart sounds include S1 (or the "first heart sound"), S2 (or "the second heart sound"), S3 (or "the third heart sound"), S4 (or "the fourth heart sound"), and their various sub-components. S1 is believed to be indicative of, among other things, mitral valve closure, tricuspid valve closure, and aortic valve opening. S2 is believed to be indicative of, among other things, aortic valve closure and pulmonary valve closure. S3 is believed to be a ventricular diastolic filling sound often indicative of certain pathological conditions, including heart failure. S4 is believed to be a ventricular diastolic filling sound resulted from atrial contraction and is believed usually indicative of pathological conditions. The term "heart sound" hereinafter refers to any indication of a heart sound (e.g., S1, S2, etc.) or any component thereof (e.g., M1 component of S1 (indicative of mitral valve closure), A2 component of S2 (indicative of aortic valve closure), P2 component of S2 (indicative of pulmonic valve closure), etc.).

A heart sound can include audible or inaudible mechanical vibrations caused by cardiac activity. In certain examples, heart sounds can be sensed with an accelerometer. Such mechanical vibrations can be conceptualized as providing acoustic energy.

The present inventors have recognized, among other things, that the maximum amplitude of a heart sound signal may not be the most desirable identifier of the heart sound. For example, a first intra heart sound energy indication and a corresponding first intra heart sound time indication for a particular heart sound of a particular heart sound waveform can be recognized, such as by using heart sound information from multiple heart sound waveforms. In an example, the first intra heart sound energy indication and the corresponding first intra heart sound time indication can be recognized using the heart sound information from the particular heart sound waveform and the heart sound information from at least one other heart sound waveform. The recognized first intra heart sound energy indication and the corresponding recognized first intra heart sound time indication can be indicative or characteristic of a desirable heart sound amplitude and timing within the particular heart sound waveform.

FIG. 1 illustrates generally an example of an illustration 100 including portions of a heart sound signal 115, including S1 120 and S2 125, shown with respect to Amplitude (mG) 110 and Time (msec) 105, where mG are units of acceleration that are produced when an accelerometer is used to measure the vibrations produced by the heart sounds.

A heart sound signal can include multiple peaks. In this example, the S1 120 portion of the heart sound signal 115 has multiple peaks, such as peak 121, peak 122, and peak 123, and the S2 125 portion of the heart sound signal 115 has multiple peaks, such as peak 126 and peak 127. In an example, the timing and amplitude of S1 can be determined using the information from the current S1, such as by selecting the largest amplitude in the S1 120 portion of the heart sound signal 115 and its corresponding timing. However, the present inventors have recognized, among other things, that the peak having the largest amplitude may not be the best identifier of the heart sound. In certain examples, a more desirable heart sound identifier can be attained using the information from the current S1, as well as information from an S1 of another heart sound cycle. In certain examples, the largest amplitude in a heart sound signal can include noise or other undesirable artifacts, or the largest amplitude may be an anomaly. In certain instances, the anomaly may contain valuable information. However, in other instances, the anomaly can undesirably influence the overall heart sound data. Thus, in certain examples, peak 121 or peak 123 and their corresponding timings could be a more desirable identifier for the S1 120 portion of the heart sound signal 115.

Figure 2:
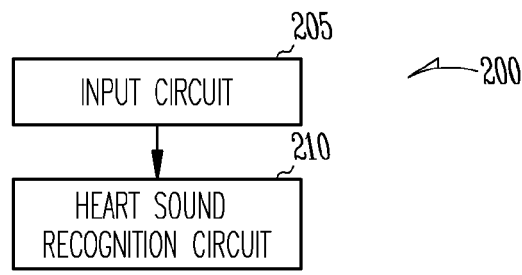
FIG. 2 illustrates generally an example of a system including an input circuit and a heart sound recognition circuit.

FIG. 2 illustrates generally an example of a system 200 including an input circuit 205 and a heart sound recognition circuit 210. The input circuit 205 can be configured to receive heart sound information. The heart sound recognition circuit 210 can be configured to recognize, within a particular heart sound of a particular heart sound waveform, a first intra heart sound energy indication and a corresponding first intra heart sound time indication. In an example, the heart sound recognition circuit 210 can recognize the first intra heart sound energy indication and the corresponding first intra heart sound time indication, such as by using the heart sound information from the particular heart sound waveform and the heart sound information from at least one other heart sound waveform.

In certain examples, the input circuit 205 can be configured to receive heart sound information from a heart sound sensor or other sensor configured to sense, detect, or otherwise collect heart sound information. In certain examples, the input circuit 205 can be configured to receive heart sound information from another device, such as an external programmer, a memory, or other device capable of having heart sound information.

The heart sound information can include any information indicative of a heart sound (e.g., the acoustic or mechanical energy of a heart). In certain examples, the heart sound information can include at least a portion of at least one heart sound signal, such as an entire heart sound signal, features of a heart sound signal, or multiple heart sound signals. The heart sound information can include at least a portion of S1 information, S2 information, S3 information, S4 information, or other heart sound information.

In this example, the heart sound recognition circuit 210 can be coupled to the input circuit 205. The heart sound recognition circuit 210 can be configured to receive information (e.g., heart sound information) from the input circuit 205. In certain examples, the heart sound recognition circuit 210 can include the input circuit 205, or the heart sound recognition circuit 210 or the input circuit 205 can be implemented using a processor, a programmer, controller, or the like.

In an example, the particular heart sound can include at least one of S1, S2, S3, S4, or other portions or components of a heart sound signal. Further, the particular heart sound can include at least a portion of one of S1, S2, S3, S4, or other portions or components of a heart sound signal, such as at least a portion of S1, the aortic valve component of S2 (commonly referred to as the A2 component of S2), the pulmonic valve component of S2 (commonly referred to as the P2 component of S2), etc.

In an example, the heart sound waveform can include at least a portion of at least one physiological cycle. Generally, the body functions in physiological cycles. In certain examples, a physiological cycle can include a cardiac cycle, a respiration cycle, or other physiological cycle of the body. The physiological cycle can be detected using an electrical signal (e.g., an electrocardiogram (ECG) or an impedance signal indicative of cardiac or respiratory activity), or the physiologic cycle can be detected using other signals, such as by using a mechanical signal (e.g., a pressure signal indicative of cardiac or respiratory activity or a heart sound signal indicative of cardiac activity). In an example, the heart sound waveform can include at least a portion of at least one physiological cycle, such as a portion of the cardiac cycle or a portion of the respiration cycle. In other examples, the heart sound waveform can include multiple physiological cycles, such as multiple cardiac cycles. In other examples, the heart sound waveform can include a specified time period, such as a 10-minute time period, or other time period.

In an example, the particular heart sound of the particular heart sound waveform can include an ensemble average of the particular heart sound over a heart sound waveform, such as that disclosed in the commonly assigned Siejko et al. U.S. Pat. No. 7,115,096 entitled "THIRD HEART SOUND ACTIVITY INDEX FOR HEART FAILURE MONITORING," which is hereby incorporated by reference in its entirety, including its disclosure of ensemble averaging an acoustic signal. In certain examples, the ensemble average of the particular heart sound over multiple heart sound waveforms can include at least a portion of the S1 (or at least a portion of an other heart sound, such as S2, S3, S4, etc.) over a heart sound waveform, such as over multiple physiological cycles (e.g., multiple cardiac cycles) or over a specified time period (e.g., 1 minute, 10 minutes, 1 hour, 1 day, etc.).

In the example of FIG. 2, the first intra heart sound energy indication and the corresponding first intra heart sound time indication can be indicative of a desirable heart sound amplitude and timing within the particular heart sound waveform. In certain examples, the desirable heart sound amplitude and timing can include a combination of the heart sound amplitude having the largest or most consistent peak, peak-to-peak, peak-to-peak with zero-crossing, or other heart sound amplitude within the particular heart sound waveform, coupled with the heart sound timing having the most consistent timing of the heart sound amplitude events (e.g., the peak, peak-to-peak, peak-to-peak with zero-crossing, or other heart sound amplitude within the particular heart sound waveform).

In an example, the first intra heart sound energy indication can include an energy (e.g., an amplitude) within the particular heart sound waveform (e.g., within the S1, S2, etc.). Similarly, the corresponding first intra heart sound time indication can include a time within the particular heart sound waveform (e.g., within the S1, S2, etc.). In certain examples, the first intra heart sound time can include the time associated with the first intra heart sound amplitude, or the first intra heart sound time can include a time different or independent from the first intra heart sound amplitude.

In an example, the particular heart sound waveform can include a current heart sound waveform. In certain examples, the system 200 can be configured to operate in real-time, or the system 200 can be configured to operate using stored data (e.g., stored or buffered heart sound information). In certain examples, the at least one other heart sound waveform can include at least one heart sound waveform occurring previous to, occurring after, or occurring at a combination of previous to or after the particular heart sound waveform. In an example, the at least one other heart sound waveform can include the immediately preceding heart sound waveform to the particular heart sound waveform.

Figure 6A:
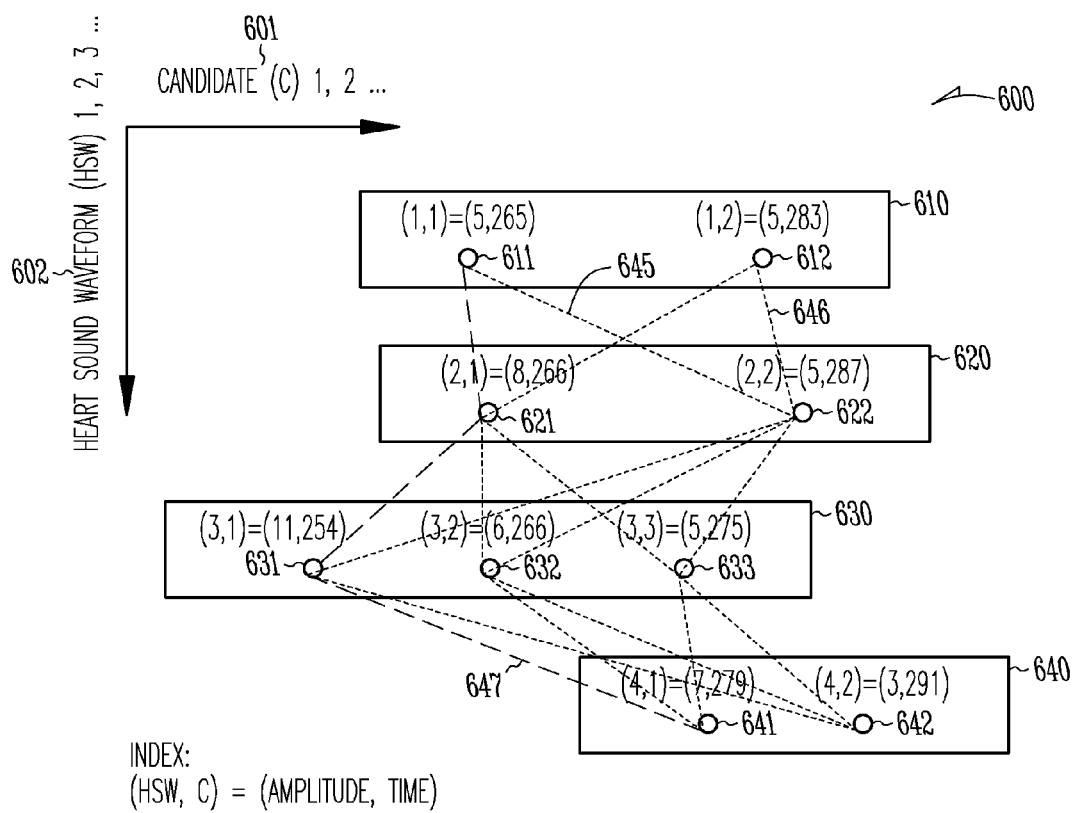
FIG. 6A illustrates generally an example of a relationship between multiple candidate heart sounds from multiple heart sound waveforms.

For example, in the example of FIG. 6A, four heart sound waveforms are displayed: a first heart sound waveform 610, a second heart sound waveform 620, a third heart sound waveform 630, and a fourth heart sound waveform 640. In an example, the particular heart sound waveform can include the third heart sound waveform 630. In this example, the at least one other heart sound waveform can include at least one of the first heart sound waveform 610, the second heart sound waveform 620, and the fourth heart sound waveform 640.

In an example, the input circuit 205 can be configured to receive S2 information. The heart sound recognition circuit 210 can be configured to recognize an intra S2 energy indication and a corresponding intra S2 time indication within the S2 of the particular heart sound waveform. In an example, the heart sound recognition circuit 210 can be configured to recognize the intra S2 energy indication and the corresponding intra S2 time indication using the S2 information from the particular heart sound waveform and also using the S2 information from at least one other heart sound waveform.

In an example, the heart sound recognition circuit 210 can be configured to recognize the first intra heart sound energy indication and the corresponding first intra heart sound time indication using a heart sound template, such as by comparing the heart sound information from the particular heart sound waveform to the heart sound template. In an example, the heart sound information can include at least one heart sound feature, such as a morphological feature. Thus, the first intra heart sound energy indication and the corresponding first intra heart sound time indication can be recognized by comparing at least one heart sound feature, such as a morphological feature, of the heart sound information from the particular heart sound waveform to the heart sound template.

In certain examples, a heart sound template can include previously attained heart sound information from a subject (e.g., a subject on which system 200 is configured to perform) or a population (e.g., one or more other subjects, such as subjects having normal cardiac health, subjects having a specific physiological condition, etc.). In an example, the heart sound information can include at least one heart sound feature, such as a morphological feature. In an example, the previously attained heart sound information can include at least a portion of the heart sound information from the at least one other heart sound waveform of the subject. In certain examples, the previously attained heart sound information can include heart sound information from a heart sound waveform that occurs previous to the particular heart sound. In certain examples, the previously attained heart sound information can include heart sound information from a heart sound waveform that occurs later in time than the particular heart sound waveform, such as when the heart sound recognition circuit 210 is recognizing using stored or buffered heart sound information.

In an example, the heart sound template can be updated using the heart sound information from the subject, such as the heart sound information from the particular heart sound waveform or the heart sound information from the at least one other heart sound waveform.

Further, in certain examples of FIG. 2, the heart sound recognition circuit 210 can be configured to recognize the first intra heart sound energy indication or the corresponding first intra heart sound time indication using a cross correlation between (1) at least a portion of the heart sound information from the particular heart sound waveform, such as at least one heart sound feature (e.g., at least one morphological feature), and (2) at least a portion of the heart sound template.

In an example, the heart sound recognition circuit 210 can be configured to produce at least one table. The table can include the recognized intra heart sound energy indication and the corresponding first intra heart sound time indication. In an example, the table can be stored in memory, and can provide a compact representation of heart sound information.

Figure 3:
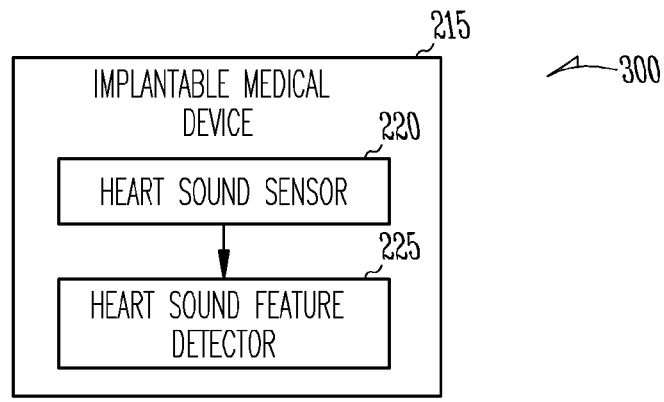
FIG. 3 illustrates generally an example of portions of a system including an implantable medical device, the implantable medical device including a heart sound sensor and a heart sound feature detector.

FIG. 3 illustrates generally an example of portions of a system 300 including an implantable medical device 215 including a heart sound sensor 220 and a heart sound feature detector 225.

In this example, the heart sound sensor 220 can be configured to sense a heart sound signal of a subject. The heart sound signal can include any signal that includes an indication of at least a portion of the at least one heart sound of the subject (e.g. S1, S2, S3, S4, or any components thereof, such as A2, P2, etc.). The heart sound sensor 220 can be configured to produce a heart sound signal, such as an electrical or optical representation of a heart sound signal, that includes information about the acoustic or vibrational heart sound signal of the subject. The heart sound sensor 220 can include any device configured to sense the heart sound signal of the subject. In certain examples, the heart sound sensor 220 can include an implantable sensor including at least one of an accelerometer, an acoustic sensor, a microphone, etc.

In an example, the heart sound sensor 220 can include an accelerometer configured to sense an acceleration signal indicative of the heart sound of the subject, such as that disclosed in the commonly assigned Carlson et al. U.S. Pat. No. 5,792,195 entitled "ACCELERATION SENSED SAFE UPPER RATE ENVELOPE FOR CALCULATING THE HEMODYNAMIC UPPER RATE LIMIT FOR A RATE ADAPTIVE CARDIAC RHYTHM MANAGEMENT DEVICE," which is hereby incorporated by reference in its entirety including its disclosure of accelerometer detection of heart sounds, or such as that disclosed in the commonly assigned Siejko et al. U.S. patent application Ser. No. 10/334,694, entitled "METHOD AND APPARATUS FOR MONITORING OF DIASTOLIC HEMODYNAMICS," filed Dec. 30, 2002 (herein "Siejko et al. '694"), which is hereby incorporated by reference in its entirety including its disclosure of accelerometer detection of heart sounds. In other examples, other accelerometer or acceleration sensor configurations can be used to sense the heart sound signal.

In another example, the heart sound sensor 220 can include an acoustic sensor configured to sense an acoustic energy indicative of the heart sound of the subject, such as that disclosed in the commonly assigned Siejko et al. '694, incorporated by reference in its entirety. In other examples, other acoustic sensor or microphone configurations can be used to sense the heart sound signal.

In the example of FIG. 3, the heart sound feature detector 225 is coupled to the heart sound sensor 220. The heart sound feature detector 225 can be configured to receive the heart sound signal from the heart sound sensor 220. The heart sound feature detector 225 can be configured to detect at least one feature of at least a portion of at least one heart sound. The heart sound feature can include at least one measurement, characteristic, morphology, computation, or interval of at least a portion of at least one heart sound. In certain examples, this includes at least one of an amplitude of a heart sound signal, a magnitude of a heart sound signal, a total energy of a heart sound signal, a peak of a heart sound signal, etc. (e.g., an amplitude or magnitude of at least one peak, at least one valley, or at least one other portion of an S1, an amplitude or magnitude of at least one peak, at least one valley, or at least one other portion of an S2, etc.).

In an example, the heart sound information used by the heart sound recognition circuit 210 can include the detected at least one heart sound feature. In certain examples, the heart sound sensor 220 can include the heart sound feature detector 225, or the heart sound feature detector 225 can include the heart sound sensor 220.

Figure 4:
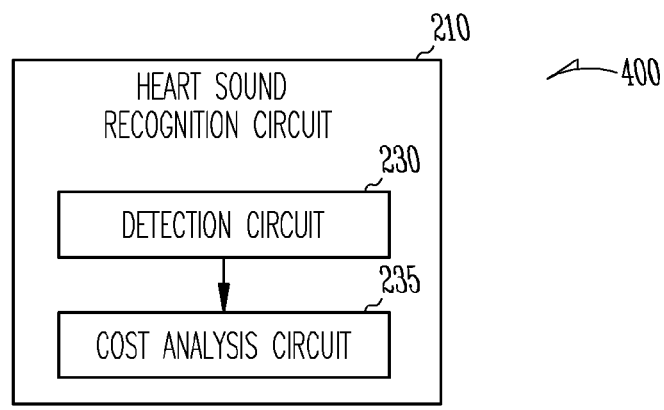
FIG. 4 illustrates generally an example of portions of a system including a heart sound recognition circuit, the heart sound recognition circuit including a detection circuit and a cost analysis circuit.

FIG. 4 illustrates generally an example of portions of a system 400 including a heart sound recognition circuit 210, the heart sound recognition circuit 210 including a detection circuit 230 and a cost analysis circuit 235.

In an example, the detection circuit 230 can be configured to detect at least one first candidate heart sound for the particular heart sound of the at least one other heart sound waveform. In an example, the detection circuit 230 can detect the at least one first candidate heart sound using the heart sound information. The at least one first candidate heart sound can include an intra heart sound energy indication and a corresponding intra heart sound time indication. In an example, the candidate heart sound can be identified or characterized, such as by using the intra heart sound energy indication and the corresponding intra heart sound time indication. A candidate heart sound can include any portion, component, or identifier of the heart sound signal, the heart sound information, or the at least one heart sound feature for a heart sound of a heart sound waveform. In an example, the first candidate heart sound can include at least one feature (e.g., a positive peak, a negative peak, etc.) of the particular heart sound of the at least one other heart sound waveform, the at least one feature having an intra heart sound energy indication associated with the at least one feature (e.g., the amplitude of the positive peak, the amplitude of the negative peak, etc.) and a corresponding intra heart sound time indication associated with the at least one feature.

In an example, the detection circuit 230 can be configured to detect at least one second candidate heart sound for the particular heart sound of the particular heart sound waveform. In an example, the detection circuit 230 can detect the at least one second candidate heart sound using the heart sound information. The at least one second candidate heart sound can include an intra heart sound energy indication and a corresponding intra heart sound time indication. In an example, the candidate heart sound can be identified or characterized using the intra heart sound energy indication and the corresponding intra heart sound time indication. In an example, the second candidate heart sound can include at least one feature (e.g., a positive peak, a negative peak, etc.) of the particular heart sound of the particular heart sound waveform, the at least one feature having an intra heart sound energy indication associated with the at least one feature (e.g., the amplitude of the positive peak, the amplitude of the negative peak, etc.) and a corresponding intra heart sound time indication associated with the at least one feature.

In the example of FIG. 4, the heart sound recognition circuit 210 can be configured to recognize the first intra heart sound energy indication and the corresponding first intra heart sound time indication using the at least one detected first candidate heart sound and the at least one detected second candidate heart sound. The first intra heart sound energy indication and the corresponding first intra heart sound time indication can be recognized using a relationship between the at least one detected first candidate heart sound and the at least one detected second candidate heart sound, such as by calculating a cost from the at least one detected first candidate heart sound to the at least one detected second candidate heart sound.

In an example, the cost analysis circuit 235 can be coupled to the detection circuit 230. The cost analysis circuit 235 can be configured to use a dynamic programming method, such as a Viterbi method or other dynamic programming method, to determine a desirable heart sound candidate for the particular heart sound waveform. In an example, the desirable heart sound candidate can include a candidate having the least cost. For example, by selecting "desirable" heart sound indications from among multiple candidates, in a manner that tends to reduce or minimizes the cost function over many cardiac cycles, the present methods can be used to track the more desirable heart sound indications.

In an example, the cost analysis circuit 235 can be configured to calculate a cost for each second candidate heart sound. In an example, the cost can be calculated for the second candidate heart sound using at least one of a jump penalty and a local score. For example, the jump penalty can include a temporal cost associated with the second candidate heart sound. In an example, the temporal cost can include a time difference between the second candidate heart sound and a first candidate heart sound (see, e.g., FIG. 6). The local score can include a local benefit associated with the at least one second candidate heart sound. In an example, the local score includes the amplitude of the second heart sound candidate. In an example, the local score or the jump penalty can be weighted (e.g., by multiplying the local score or the jump penalty by a scaling factor) to further tailor the cost analysis.

In an example, the heart sound recognition circuit 210 can be configured to recognize the first intra heart sound energy indication and the corresponding first intra heart sound time indication using the calculated cost, such as by selecting the heart sound candidate for the particular heart sound waveform having a lowest cost or a highest benefit.

In an example, the cost analysis can include a total score. The total score can factor in at least one of the jump penalty for a candidate heart sound having a temporal cost and the local score for the candidate heart sound having a local benefit. In an example, the total score ("D(t, x)") can be calculated by taking the difference of the jump penalty ("J(x', x)") from a previous total score ("D(t−1, x')"), and by adding the local score ("d($X_t$, x)") to the maximum result of the difference:

$$D(t, x) = \max_{x' \in M(x)} \{D(t-1, x') - J(x', x)\} + d(X_t, x), \quad \text{(Eq. 1)}$$

wherein t denotes a heart sound waveform, x denotes a candidate heart sound, and M(x) includes a set of possible predecessors of x.

In an example, the heart sound recognition circuit 210 can be configured to calculate a back pointer. In an example, the back pointer can indicate a pointer from the at least one second candidate heart sound to a desirable at least one first candidate heart sound. The desirable at least one first candidate heart sound typically includes the first candidate heart sound having a maximum result of the difference between the previous total score and the current jump penalty. Thus, in an example, the back pointer ("B(t, x)") can be calculated using:

$$B(t, x) = \underset{x' \in M(x)}{\mathrm{argmax}} \{D(t-1, x') - J(x', x)\}. \quad \text{(Eq. 2)}$$

Figure 5:
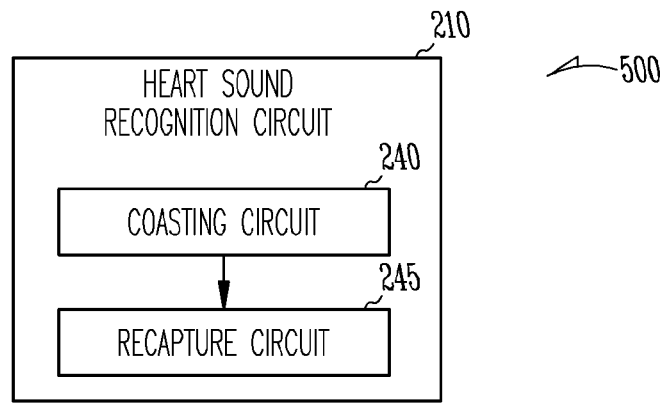
FIG. 5 illustrates generally an example of portions of a system including a heart sound recognition circuit, the heart sound recognition circuit including a coasting circuit and a recapture circuit.

FIG. 5 illustrates generally an example of portions of a system 500 including a heart sound recognition circuit 210 including a coasting circuit 240 and, if desired, also including a recapture circuit 245.

In an example, the coasting circuit 240 can be coupled to the heart sound recognition circuit 210. The coasting circuit 240 can be configured to disregard the recognized first intra heart sound energy indication and the corresponding recognized first intra heart sound time indication. In an example, if the calculated cost of a recognized first intra heart sound energy indication and corresponding first intra heart sound time indication is too high (e.g., above a threshold, or above previous results), or if the total score of the recognized first intra heart sound energy indication and corresponding first intra heart sound time indication is too low (e.g., below a threshold, or below previous results), then the coasting circuit 240 can be configured to disregard the recognized first intra heart sound energy indication and corresponding first intra heart sound time indication.

The coasting circuit 240 can be configured to coast (e.g., disregard heart sound indications that would otherwise be recognized) for a certain period (e.g., a certain number of heart sound waveforms, a certain period of time, etc.). In an example, if, at the end of the certain period, the calculated cost remains too high, or if the total score remains too low, the coasting circuit 240 will stop coasting, if so configured. Generally, if the end of the certain period is reached with the calculated cost still too high, or the total score still too low, this can be an indication that the heart sound information has changed or a problem has arisen (e.g., noise, physical condition change, system failure, etc.). In an example, if the calculated cost remains too high, or if the total score remains too low, at the end of the certain period the coasting circuit 240 can provide a notification to a user, if so configured, such as by using a notification circuit.

In an example, the coasting circuit 240 can be configured to disregard the recognized first intra heart sound energy indication and the corresponding recognized first intra heart sound time indication based upon a result of a comparison. In an example, the comparison can include a comparison of the recognized first intra heart sound energy indication and the corresponding recognized first intra heart sound time indication and at least one other recognized intra heart sound energy indication and a corresponding at least one other recognized intra heart sound time indication within the particular heart sound of at least one other heart sound waveform.

In an example, the recapture circuit 245 can be coupled to the coasting circuit 240 to provide a storage buffer for the disregarded information before discarding, so that it can be recaptured, if desired. Generally, the recapture circuit 245 can be configured to recapture the disregarded recognized first intra heart sound energy indication and the corresponding disregarded recognized first intra heart sound time indication. In an example, if a recognized first intra heart sound energy indication and a corresponding recognized first intra heart sound time indication have been disregarded, such as by using the coasting circuit 240, and the coasting circuit 240 recurrently reaches the end of the certain period, then it may be beneficial to recapture the disregarded recognized first intra heart sound energy indication and the corresponding recognized first intra heart sound time indication (e.g., it may be beneficial if the heart sound information has changed, if the subject's status has changed, etc.).

In an example, the recapture circuit 245 can be configured to recapture the disregarded recognized first intra heart sound energy indication and the corresponding disregarded recognized first intra heart sound time indication, with the recapture triggered using a comparison. In an example, the comparison can include a comparison of the disregarded recognized first intra heart sound energy indication and the corresponding disregarded recognized first intra heart sound time indication and at least one other recognized intra heart sound energy indication and a corresponding at least one other recognized intra heart sound time indication within the particular heart sound of at least one other heart sound waveform.

FIG. 6A illustrates generally an example, using exemplary data, of a relationship 600 between multiple candidate heart sounds 611, 612, 621, 622, 631, 632, 633, 641, 642 from multiple heart sound waveforms (the first heart sound waveform 610, the second heart sound waveform 620, the third heart sound waveform 630, and the fourth heart sound waveform 640), shown with respect to candidates 601 and heart sound waveform 602. In this example, the candidate heart sound 611 can be identified as candidate heart sound (1,1) 611, where (1,1) refers to (heart sound waveform, candidate number of the heart sound waveform). Each candidate heart sound (e.g., candidate heart sound (1,1) 611) is shown with its amplitude (rounded up to the nearest whole number) and corresponding time (e.g., candidate heart sound (1,1) 611 has a rounded amplitude of 5 and a corresponding time index of 265, (5,265)).

The relationship 600 illustrates an example of four heart sound waveforms, each having at least two candidate heart sounds. In an example, Table 1 (below) generally illustrates examples of calculated jump penalties associated with each candidate. In this example, the jump penalty is indicative of the temporal distance between a heart sound candidate of a particular heart sound waveform (e.g., the second heart sound waveform 620) and a heart sound candidate of the immediately preceding heart sound waveform to the particular heart sound waveform (e.g., the first heart sound waveform 610).

TABLE 1

| | J = jump penalty | | |
|---|---|---|---|
| (HSW, Candidate) | 1 | 2 | 3 |
| 1 | 0 | 0 | |
| 2 | 1, 17 | 22, 4 | |
| 3 | 12, 33 | 0, 21 | 9, 12 |
| 4 | 25, 13, 4 | 37, 25, 16 | |

In Table 1, the candidate heart sound (1,1) 611 and the candidate heart sound (1,2) 612 are initially given jump penalties of zero, because there is no data preceding them. Further, relationship 600 shows jump paths 645, 646. The jump path 645 is a jump path from the candidate heart sound (1,1) 611 to the candidate heart sound (2,2) 622. In Table 1, the jump path 645 is displayed in row 2, column 2, having a value of 22, which is representative of a shift in the time index from 265 to 287. The jump path 646 is a jump path from the candidate heart sound (1,2) 612 to the candidate heart sound (2,2) 622.

In an example, Table 2 (below) generally illustrates the calculated total scores associated with each candidate of relationship 600 in accordance with Eq. 1, where the local score ("$d(X_t,x)$") includes the amplitude of the candidate and a gain. In this example, the gain of the local score is 5.

TABLE 2

| $D(t, x) = \max_{x' \in M(x)} \{D(t-1, x') - J(x', x)\} + d(X_t, x)$ | | | |
|---|---|---|---|
| (HSW, Candidate) | 1 | 2 | 3 |
| 1 | 0 | 0 | |
| 2 | 39 | 21 | |
| 3 | 82 | 69 | 55 |
| 4 | 92 | 60 | |

In an example, Table 3 (below) generally illustrates the calculated back pointer for each candidate of relationship 600 in accordance with Eq. 2.

TABLE 3

| $B(t, x) = \arg\max_{x' \in M(x)} \{D(t-1, x') - J(x', x)\}$ | | | |
|---|---|---|---|
| (HSW, Candidate) | 1 | 2 | 3 |
| 1 | 0 | 0 | |
| 2 | 1 | 2 | |
| 3 | 1 | 1 | 1 |
| 4 | 1 | 1 | |

FIG. 6A also includes a traceback path 647. In an example, the traceback path 647 can be determined using the calculated back pack pointers. In an example, a candidate was chosen at the fourth heart sound waveform 640, such as by choosing the candidate having the highest total score. In this example, the candidate heart sound (4,1) 641 was chosen to start the traceback path. The traceback path goes to the first candidate of the previous heart sound waveform, the candidate heart sound (3,1) 631, using the back pointer calculated for the candidate heart sound (4,1) 641, 1. Similarly, the traceback path continues to the first candidate of the second heart sound waveform, the candidate heart sound (2,1) 621, using the back pointer calculated for the candidate heart sound (3,1) 631, 1, and so on.

Figure 6B:
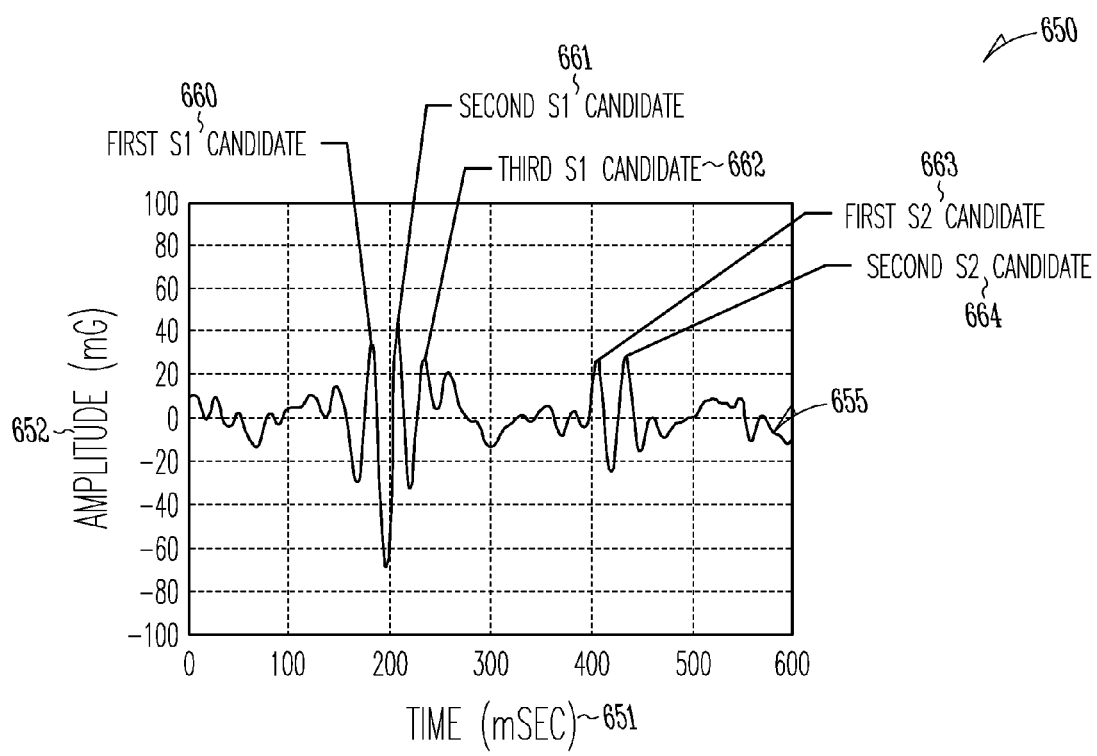
FIG. 6B illustrates generally an example of an illustration including a heart sound signal and multiple heart sound candidates.

FIG. 6B illustrates generally an example of an illustration 650 including a heart sound signal 655, shown with respect to Amplitude (mG) 652 and Time (msec) 651, and including multiple heart sound candidates. In this example, the multiple heart sound candidates include a first S1 candidate 660, a second S1 candidate 661, a third S1 candidate 662, a first S2 candidate 663, and a second S2 candidate 664.

In an example, the at least one first candidate heart sound for the particular heart sound of the at least one particular heart sound waveform can include (1) (for the S1 of the current heart sound cycle shown in the illustration 650) the first S1 candidate 660, the second S1 candidate 661, and the third S1 candidate 662, or (2) (for the S2 of the current heart sound cycle shown in the illustration 650) the first S2 candidate 663 and the second S2 candidate 664.

For example, in a relationship similar to the relationship 600 of FIG. 6A showing S1 candidates with respect to heart sound waveforms, where the heart sound cycle of the illustration 650 is a heart sound waveform (e.g., a first heart sound waveform), the first S1 candidate 660 would be the first candidate of the heart sound waveform (e.g., candidate heart sound (1,1)), the second S1 candidate 661 would be the second candidate of the heart sound waveform (e.g., candidate heart sound (1,2)), and the third S1 candidate 662 would be the third candidate of the heart sound waveform (e.g., candidate heart sound (1,3)).

Figure 6C:
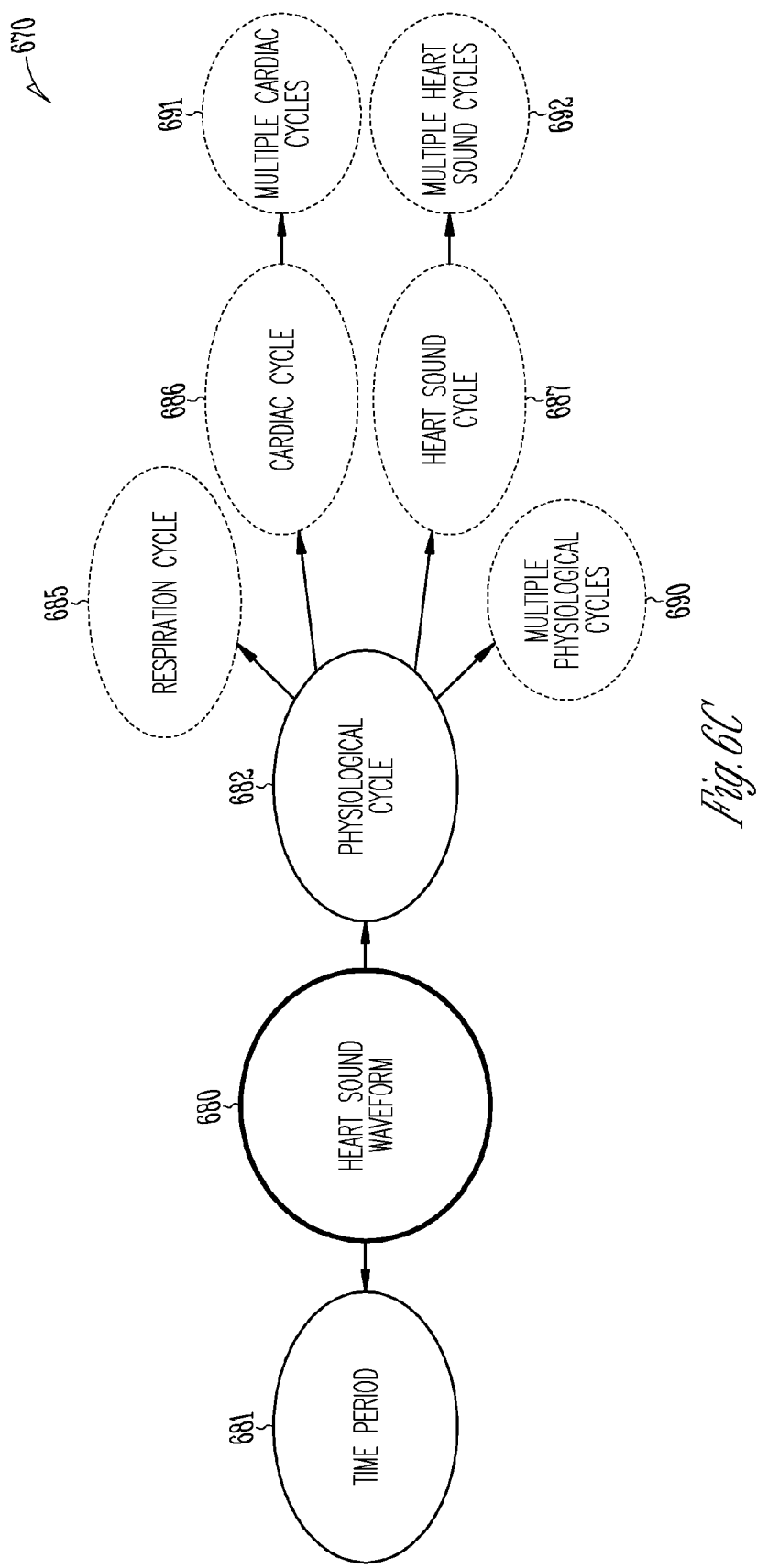
FIG. 6C illustrates generally a diagram including a heart sound waveform and exemplary heart sound waveforms.

FIG. 6C illustrates generally a diagram 670 including a heart sound waveform 680 and exemplary heart sound waveforms. The exemplary heart sound waveforms include a time period 681 and a physiological cycle 682. The physiological cycle 682 includes multiple physiological cycles 690, a respiration cycle 685, a cardiac cycle 686, multiple cardiac cycles 691, a heart sound cycle 687, and multiple heart sound cycles 692. In other examples, the heart sound waveform can include at least a portion of one physiological cycle, including at least a portion of one cardiac cycle, etc. The heart sound waveform can also include multiple respiration cycles.

Figure 7:
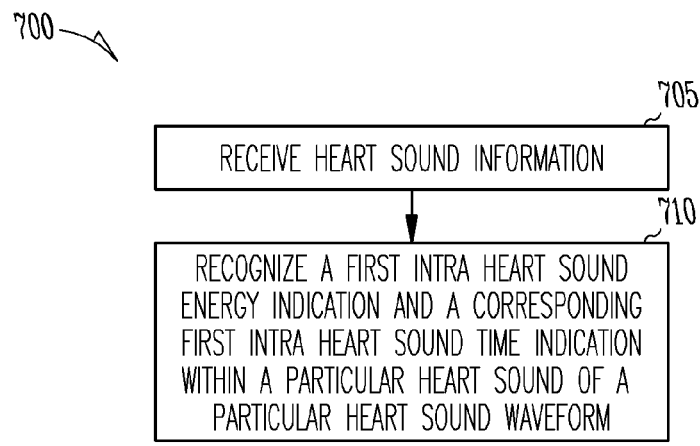
FIG. 7 illustrates generally an example of a method including receiving heart sound information and recognizing a first intra heart sound energy indication and a corresponding first intra hear sound time indication within a particular heart sound of a particular heart sound waveform.

FIG. 7 illustrates generally an example of a method 700 including receiving heart sound information and recognizing a first intra heart sound energy indication and a corresponding first intra heart sound time indication within a particular heart sound of a particular heart sound waveform. In an example, the first intra heart sound energy indication and the corresponding first intra heart sound time indication can be recognized using the heart sound recognition circuit 210.

At 705, heart sound information can be received, such as by using the input circuit 205.

At 710, a first intra heart sound energy indication and a corresponding first intra heart sound time indication can be recognized within a particular heart sound of a particular heart sound waveform. In an example, at 710, the first intra heart sound energy indication and the corresponding first intra heart sound time indication can be recognized using the heart sound information from the particular heart sound waveform and the heart sound information from at least one other heart sound waveform.

In an example, the recognizing the first intra heart sound energy indication and the corresponding first intra heart sound time indication within the particular heart sound includes recognizing within at least a portion of one of S1, S2, S3, S4, or other portions or components of a heart sound signal. In an example, the recognizing the first intra heart sound energy indication and the corresponding first intra heart sound time indication can correspond to the at least a portion of one of S1, S2, S3, S4, or other portions or components of the heart sound signal.

In the example of method 700, receiving the heart sound information can include receiving S2 information. The recognizing the first intra heart sound energy indication and the corresponding first intra heart sound time indication within the particular heart sound of the particular heart sound waveform can include recognizing an intra S2 energy indication and a corresponding intra S2 time indication within an S2 of the particular waveform. Further, the using the heart sound information from the particular heart sound waveform and the heart sound information from the at least one other heart sound waveform can include using the S2 information from the particular heart sound waveform and the S2 information from at least on other heart sound waveform.

In an example, the recognizing the first intra heart sound energy indication and the corresponding first intra heart sound time indication can include using a heart sound template. In an example, the using the heart sound template can include comparing the heart sound information from the particular heart sound waveform to the heart sound template. In certain examples, the heart sound information from the particular heart sound waveform can include at least one heart sound feature, such as a morphological feature. In an example, the using the heart sound template can include using a cross correlation between at least a portion of the heart sound information from the particular heart sound waveform and at least a portion of the heart sound template. In an example, the using the cross correlation can include using a cross correlation between a morphology of the heart sound signal from the particular heart sound waveform and at least a portion of the heart sound template, where the morphology includes multiple heart sound features, measurements, characteristics, etc., of the heart sound signal from the particular heart sound waveform.

In an example, the heart sound template can be updated using at least a portion of the heart sound information. In certain examples, the using the at least a portion of the heart sound information can include using at least a portion of the heart sound information from the at least one other heart sound waveform.

Figure 8:
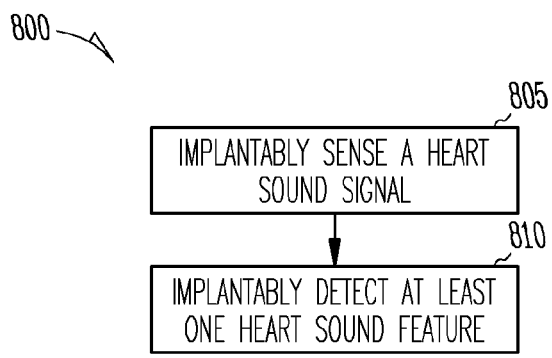
FIG. 8 illustrates generally an example of portions of a method including implantably sensing a heart sound signal and implantably detecting at least one heart sound feature.

FIG. 8 illustrates generally an example of portions of a method 800 including implantably sensing a heart sound signal and implantably detecting at least one heart sound feature. In an example, the heart sound signal can be implantably sensed using the heart sound sensor 220. In an example the at least one heart sound feature can be detected using the heart sound feature detector 225.

At 805, a heart sound signal can be implantably sensed. The heart sound signal can include any signal indicative of at least a portion of the at least one heart sound of the subject (e.g. S1, S2, S3, S4, or any components thereof, such as A2, P2, etc.) In an example, the heart sound signal can be sensed using the heart sound sensor 220.

At 810, at least one heart sound feature can be implantably detected. The at least one heart sound feature can be detected using the heart sound signal. Generally, the at least one heart sound feature can include at least one measurement, characteristic, morphology, computation, or interval of at least a portion of at least one heart sound.

Figure 9:
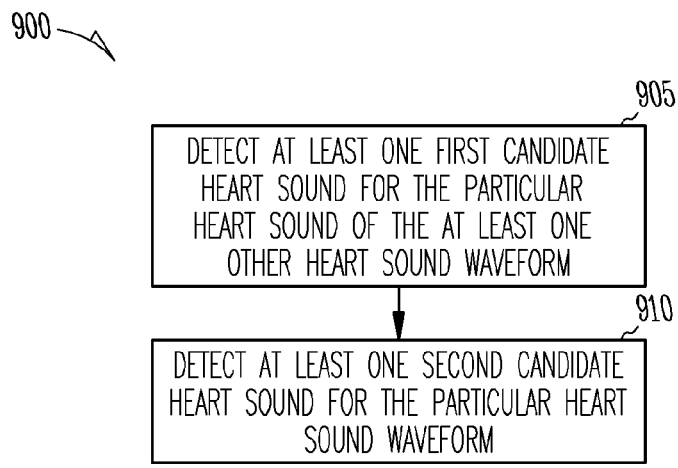
FIG. 9 illustrates generally an example of portions of a method including detecting at least one candidate heart sound for the particular heart sound of the particular heart sound waveform and the at least one other heart sound waveform.

FIG. 9 illustrates generally an example of portions of a method 900 including detecting at least one candidate heart sound for the particular heart sound of the particular heart sound waveform and the at least one other heart sound waveform. In an example, the at least one candidate heart sound can be detected using the detection circuit 230.

At 905, at least one first candidate heart sound for the particular heart sound of the at least one other heart sound waveform can be detected. In an example, the at least one first candidate heart sound can be detected using the heart sound information. The detecting the at least one first candidate heart sound can include detecting an intra heart sound energy indication and a corresponding intra heart sound time indication. Generally, the at least one other heart sound waveform excludes the particular heart sound waveform. In an example, the at least one other heart sound waveform can include the immediately preceding heart sound waveform to the particular heart sound waveform. In other examples, the at least one other heart sound waveform can include other preceding heart sound waveforms to the particular heart sound waveform, or the at least one other heart sound waveform can include heart sound waveforms occurring later in time than the particular heart sound waveform.

At 910, at least one second candidate heart sound for the particular heart sound of the particular heart sound waveform can be detected. In an example, the at least one second candidate heart sound can be detected using the heart sound information. The detecting the at least one second candidate heart sound can include detecting an intra heart sound energy indication and a corresponding intra heart sound time indication.

In an example, the method 900 can further include recognizing the first intra heart sound energy indication and the corresponding first intra heart sound time indication using the at least one detected first candidate heart sound and the at least one detected second candidate heart sound.

Figure 10:
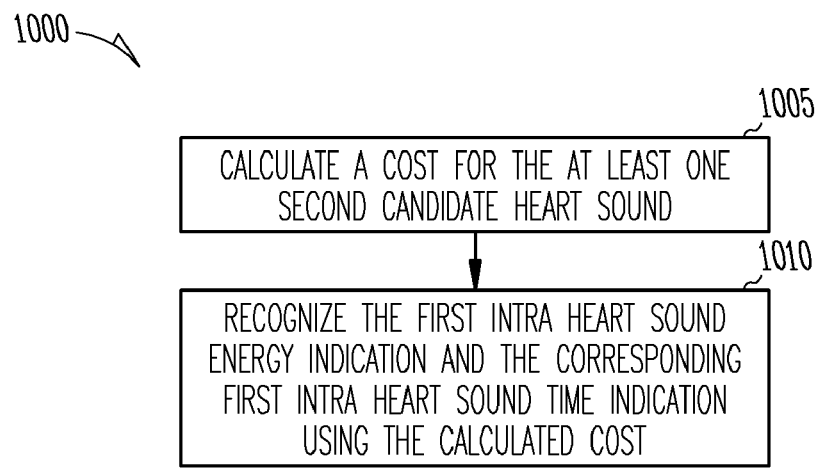
FIG. 10 illustrates generally an example of portions of a method including calculating a cost for at least one candidate heart sound and recognizing the first intra heart sound energy indication and the corresponding first intra heart sound time indication using the calculated cost.

FIG. 10 illustrates generally an example of portions of a method 1000 including calculating a cost for at least one candidate heart sound and recognizing the first intra heart sound energy indication and the corresponding first intra heart sound time indication using the calculated cost. By calculating the cost of the at least one candidate heart sound, a desirable heart sound candidate for a particular heart sound waveform can be determined. In certain examples, the calculating the cost includes using a dynamic programming method, such as the Viterbi method or other dynamic programming method. In certain examples, the cost can be calculated using the cost analysis circuit 235, and the first intra heart sound energy indication and the corresponding first intra heart sound time indication can be recognized using the heart sound recognition circuit 210.

At 1005, a cost can be calculated for the at least one second candidate heart sound. The calculating the cost can include at least one of calculating a jump penalty and calculating a local score. Calculating the jump penalty can include calculating a temporal cost associated with the at least one second candidate heart sound. In an example, calculating the jump penalty can include calculating the time difference between the second candidate heart sound and a first candidate heart sound. Typically, calculating the local score can include calculating a local benefit associated with the at least one second candidate heart sound. In an example, calculating the local score can include calculating the amplitude of the second candidate heart sound. In other examples, the calculating the jump penalty or the calculating the local score can include weighting the calculating to improve or optimize the cost calculation.

In an example, calculating the cost can include calculating a total score. Calculating the total score can include reducing a previous total score by the jump penalty, and then adding the local score to the maximum result of the reduced previous total score. (See, e.g., Eq. 1).

At 1010, the first intra heart sound energy indication and the corresponding first intra heart sound time indication can be recognized using the calculated cost. In an example, the recognizing the first intra heart sound energy indication and the corresponding first intra heart sound time indication can include recognizing the candidate heart sound having the least cost, or the maximum total score.

In other examples, once the first intra heart sound energy indication and the corresponding first intra heart sound time indication have been recognized, they can be stored, such as stored in a table, or stored in memory.

Figure 11:
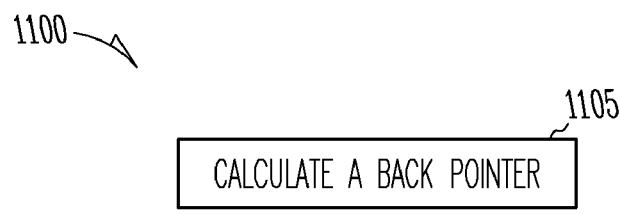
FIG. 11 illustrates generally an example of portions of a method including calculating a back pointer.

FIG. 11 illustrates generally an example of portions of a method 1100 including calculating a back pointer. In an example, the back pointer can be calculated using the heart sound recognition circuit 210. At 1105, a back pointer can be calculated. Generally, the back pointer can be indicative of the lowest cost path through multiple heart sound candidates of multiple heart sound waveforms.

In an example, the calculating the back pointer can include selecting the candidate heart sound having the maximum difference between the previous total score of the candidate heart sound and the current jump penalty. (See, e.g., Eq. 2).

Figure 12:
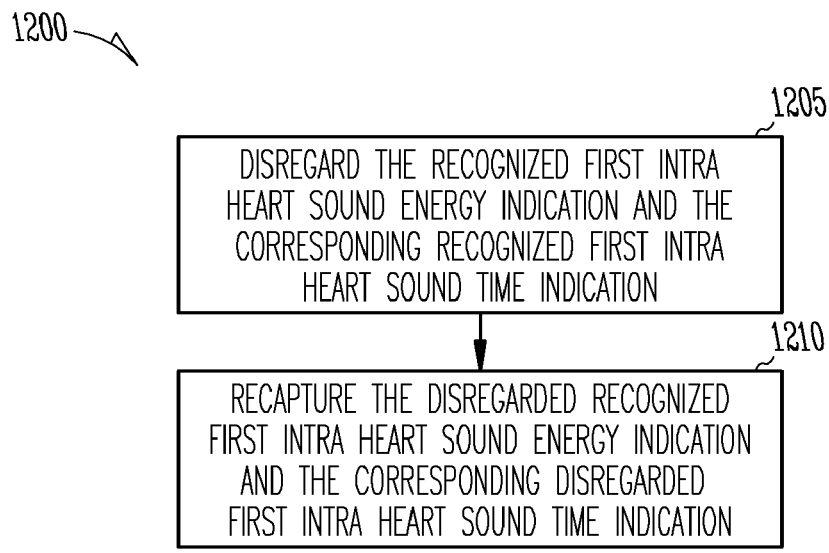
FIG. 12 illustrates generally an example of portions of a method including disregarding the recognized first intra heart sound energy indication and the corresponding recognized first intra heart sound time indication and recapturing the disregarded recognized first intra heart sound energy indication and the corresponding disregarded recognized first intra heart sound time indication.

FIG. 12 illustrates generally an example of portions of a method 1200 including disregarding the recognized first intra heart sound energy indication and the corresponding recognized first intra heart sound time indication and recapturing the disregarded recognized first intra heart sound energy indication and the corresponding disregarded recognized first intra heart sound time indication. In certain examples, the recognized first intra heart sound energy indication and the corresponding recognized first intra heart sound time indication can be disregarded using the coasting circuit 240, and the disregarded recognized first intra heart sound energy indication and the corresponding disregarded recognized first intra heart sound time indication can be recaptured using the recapture circuit 245.

In certain examples, if the heart sound information from a particular heart sound waveform is different than the heart sound information from previous heart sound waveforms, then the different heart sound information can be disregarded, e.g., by skipping over the recognized first intra heart sound energy indication and the corresponding recognized first intra heart sound time indication for that particular heart sound waveform. Similarly, if the heart sound information continues to be different, a buffered version of the disregarded recognized first intra heart sound energy indication and corresponding disregarded recognized first intra heart sound time indication can be recaptured.

At 1205, the recognized first intra heart sound energy indication and the corresponding recognized first intra heart sound time indication can be disregarded. Generally, if the calculated cost of a recognized first intra heart sound energy indication and corresponding first intra heart sound time indication is too high (e.g., above a threshold, or above previous results), or if the total score of the recognized first intra heart sound energy indication and corresponding first intra heart sound time indication is too low (e.g., below a threshold, or below previous results), then the recognized first intra heart sound energy indication and corresponding first intra heart sound time indication can be disregarded.

In an example, the recognized first intra heart sound energy indication and the corresponding recognized first intra heart sound time indication can be disregarded for a certain period (e.g., a certain number of heart sound waveforms, a certain period of time, etc.). In an example, if, at the end of the certain period, the calculated cost remains too high, or if the total score remains too low, the disregarding can cease. This can be indicative of a change (e.g., physical change, physiological change, system failure, environmental change, etc.). In an example, once it is determined that the heart sound information is relatively consistent (e.g., after disregarding for the certain period), the information should no longer be disregarded.

In an example, the recognized first intra heart sound energy indication and the corresponding recognized first intra heart sound time indication can be disregarded, with the disregarding triggered using a comparison. The using the comparison can include using a comparison of the recognized first intra heart sound energy indication and the corresponding recognized first intra heart sound time indication and at least one other recognized intra heart sound energy indication and a corresponding at least one other recognized intra heart sound time indication within the particular heart sound of at least one other heart sound waveform.

At 1210, the disregarded recognized first intra heart sound energy indication and the corresponding disregarded recognized first intra heart sound time indication can be recaptured. In an example, if the disregarding occurs for the certain period, then it may be beneficial to recapture the disregarded recognized first intra heart sound energy indication and the corresponding recognized first intra heart sound time indication (e.g., it may be beneficial if the heart sound information has changed, if the subject's status has changed, etc.). In an example, if the disregarding occurs for a period shorter than the certain period (e.g., the heart sound information is different for only a short time, such as one heart sound waveform), then it may not be beneficial to recapture the disregarded recognized first intra heart sound energy indication and the corresponding disregarded recognized first intra heart sound time indication (e.g., the disregarded information can consist of noise or useless data).

In an example, the disregarded recognized first intra heart sound energy indication and the corresponding disregarded recognized first intra heart sound time indication can be recaptured, with the recapturing triggered using a comparison. The comparison can include a comparison of the disregarded recognized first intra heart sound energy indication and the corresponding disregarded recognized first intra heart sound time indication and at least one other recognized intra heart sound energy indication and a corresponding at least one other recognized intra heart sound time indication within the particular heart sound of at least one other heart sound waveform.

Figure 13:
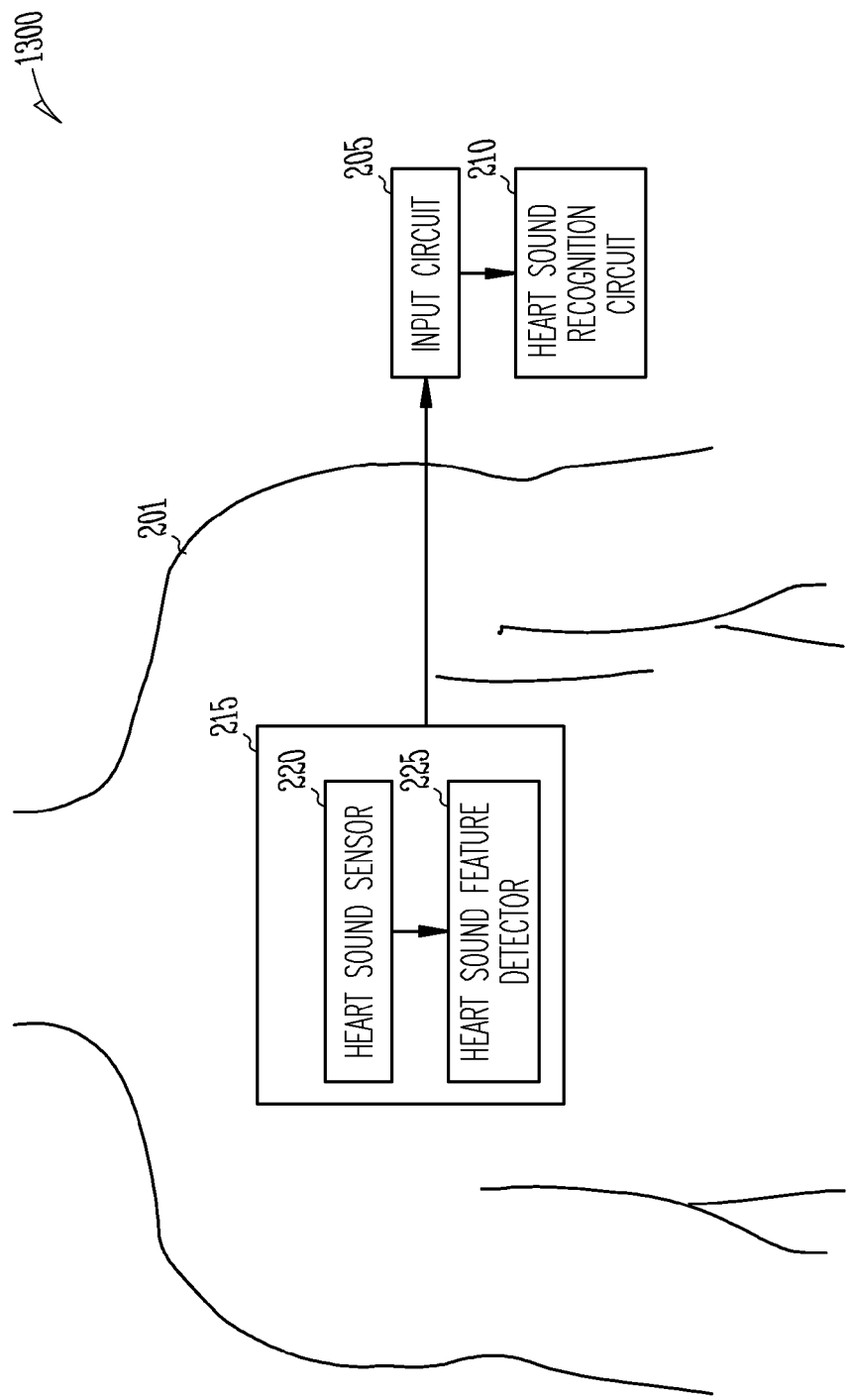
FIG. 13 illustrates generally an example of a system including an implantable medical device, an input circuit, and a heart sound recognition circuit. The implantable medical device includes a heart sound sensor and a heart sound feature detector.

FIG. 13 illustrates generally an example of a system 1300 including an implantable medical device 215, an input circuit 205, and a heart sound recognition circuit 210. The implantable medical device 215 can include a heart sound sensor 220 and a heart sound feature detector 225. In certain examples, the implantable medical device 215 can include an implantable cardiac rhythm management (CRM) device, such as a pacer, defibrillator, cardiac resynchronization therapy (CRT) or other such CRM device. In this example, the implantable medical device 215 is implanted in a subject 201. Generally, the heart sound sensor 220 can be configured to sense a heart sound signal of the subject 201. The heart sound feature detector 225 is coupled to the heart sound sensor 220 and can be configured to receive the heart sound signal from the heart sound sensor 220. In an example, the heart sound feature detector 225 can be configured to detect at least one feature of at least a portion of at least one heart sound.

In an example, the input circuit 205 can be communicatively coupled to the implantable medical device 215, and can be configured to receive heart sound information from the heart sound sensor 220, or at least one heart sound feature from the heart sound feature detector 225. In an example, the heart sound recognition circuit 210 is coupled to the input circuit 205, and can be configured to receive heart sound information from the input circuit 205. Generally, the heart sound recognition circuit 210 can be configured to recognize, within a particular heart sound of a particular heart sound waveform, a first intra heart sound energy indication and a corresponding first intra heart sound time indication using the heart sound information from the particular heart sound waveform and the heart sound information from at least one other heart sound waveform.

The recognized first intra heart sound energy indication and the corresponding recognized first heart sound time indication can be used to detect heart failure (HF) decompensation. In an example, an improved S3 amplitude and timing recognition can provide earlier HF decompensation detection than other HF decompensation detection methods (e.g., thoracic impedance HF decompensation detection).

In the examples of FIG. 1-13, various examples, including receiving heart sound information, recognizing a first intra heart sound energy indication and a corresponding first intra heart sound time indication, implantable sensing a heart sound signal, implantable detecting at least one heart sound feature, detecting at least one heart sound candidate, calculating a cost for the at least one heart sound candidate, calculating a back pointer, disregarding the recognized first intra heart sound energy indication and the corresponding recognized first intra heart sound time indication, or recapturing the disregarded recognized first intra heart sound energy indication and the corresponding disregarded recognized first intra heart sound time indication, are disclosed. It is to be understood that these examples are not exclusive, and can be implemented either alone or in combination, or in various permutations or combinations.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. A system, comprising:
an input circuit, configured to receive heart sound information;
a heart sound recognition circuit, coupled to the input circuit, configured to recognize, within a particular heart sound of a particular heart sound waveform, a first intra heart sound energy indication and a corresponding first intra heart sound time indication using the heart sound information from the particular heart sound waveform and the heart sound information from at least one other heart sound waveform;
wherein the particular heart sound of the particular heart sound waveform includes an ensemble averaged heart sound over multiple physiological cycles;
wherein the particular heart sound includes at least a portion of one of S1, S2, S3, and S4; and
wherein the first intra heart sound energy indication and the corresponding first intra heart sound time indication corresponds to the at least a portion of one of S1, S2, S3, and S4, respectively.

2. The system of claim 1, wherein the input circuit is configured to receive S2 information; and
wherein the heart sound recognition circuit is configured to recognize, within the S2 of the particular heart sound waveform, an intra S2 energy indication and a corresponding intra S2 time indication using the S2 information from the particular heart sound waveform and the S2 information from at least one other heart sound waveform.

3. The system of claim 1, wherein each physiological cycle of the multiple physiological cycles includes a cardiac cycle.

4. The system of claim 1, wherein the at least one other heart sound waveform includes an immediately preceding heart sound waveform to the particular heart sound waveform.

5. The system of claim 1, wherein the heart sound recognition circuit is configured to recognize the first intra heart sound energy indication and the corresponding first intra heart sound time indication using a heart sound template.

6. The system of claim 5, wherein the heart sound template includes at least a portion of the heart sound information from the at least one other heart sound waveform.

7. The system of claim 6, wherein the heart sound recognition circuit is configured to recognize the first intra heart sound energy indication and the corresponding first intra heart sound time indication using a cross correlation between at least a portion of the heart sound information from the particular heart sound waveform and at least a portion of the heart sound template.

8. The system of claim 1, including:
an implantable medical device, the implantable medical device including:
a heart sound sensor, configured to sense a heart sound signal; and
a heart sound feature detector, coupled to the heart sound sensor, the heart sound feature detector configured to detect at least one heart sound feature using the heart sound signal; and
wherein the heart sound information includes the at least one heart sound feature.

9. The system of claim 1, wherein the heart sound recognition circuit includes a detection circuit, the detection circuit configured to:

detect at least one first candidate heart sound for the particular heart sound of the at least one other heart sound waveform using the heart sound information, wherein the at least one first candidate heart sound includes an intra heart sound energy indication and a corresponding intra heart sound time indication; and
detect at least one second candidate heart sound for the particular heart sound of the particular heart sound waveform using the heart sound information, wherein the at least one second candidate heart sound includes an intra heart sound energy indication and a corresponding intra heart sound time indication; and
wherein the heart sound recognition circuit is configured to recognize the first intra heart sound energy indication and the corresponding first intra heart sound time indication using:
the at least one detected first candidate heart sound; and
the at least one detected second candidate heart sound.

10. The system of claim 9, wherein the at least one other heart sound waveform includes an immediately preceding heart sound waveform to the particular heart sound waveform.

11. The system of claim 9, wherein the heart sound recognition circuit includes a cost analysis circuit, coupled to the detection circuit, the cost analysis circuit configured to calculate a cost for the at least one second candidate heart sound, the calculated cost including:
a jump penalty indicative of a temporal cost associated with the at least one second candidate heart sound; and
a local score indicative of a local benefit associated with the at least one second candidate heart sound; and
wherein the heart sound recognition circuit is configured to recognize the first intra heart sound energy indication and the corresponding first intra heart sound time indication using the calculated cost.

12. The system of claim 11, wherein the heart sound recognition circuit is configured to calculate a back pointer that indicates a pointer from the at least one second candidate heart sound to an optimal at least one first candidate heart sound using the cost analysis.

13. The system of claim 1, wherein the heart sound recognition circuit includes a coasting circuit, coupled to the heart sound recognition circuit, configured to disregard the recognized first intra heart sound energy indication and the corresponding recognized first intra heart sound time indication using a comparison of:
the recognized first intra heart sound energy indication and the corresponding recognized first intra heart sound time indication; and
at least one other recognized intra heart sound energy indication and a corresponding at least one other recognized intra heart sound time indication within the particular heart sound of at least one other heart sound waveform.

14. The system of claim 13, wherein the heart sound recognition circuit includes a recapture circuit, coupled to the coasting circuit, configured recapture the disregarded recognized first intra heart sound energy indication and the corresponding disregarded recognized first intra heart sound time indication using a comparison of:
the disregarded recognized first intra heart sound energy indication and the corresponding disregarded recognized first intra heart sound time indication; and
at least one other recognized intra heart sound energy indication and a corresponding at least one other recognized intra heart sound time indication within the particular heart sound of at least one other heart sound waveform.

15. A system, comprising:
- means for receiving heart sound information;
- means for recognizing a first intra heart sound energy indication and a corresponding first intra heart sound time indication within a particular heart sound of a particular heart sound waveform using the heart sound information from the particular heart sound waveform and the heart sound information from at least one other heart sound waveform; and
- wherein the particular heart sound of the particular heart sound waveform includes an ensemble averaged heart sound over multiple physiological cycles.

16. The system of claim 15, including:
- means for disregarding the recognized first intra heart sound energy indication and the corresponding recognized first intra heart sound time indication.

17. The system of claim 16, including:
- means for recapturing the disregarded recognized first intra heart sound energy indication and the corresponding disregarded recognized first intra heart sound time indication.

18. A method, comprising:
- receiving heart sound information;
- recognizing a first intra heart sound energy indication and a corresponding first intra heart sound time indication within a particular heart sound of a particular heart sound waveform using the heart sound information from the particular heart sound waveform and the heart sound information from at least one other heart sound waveform;
- wherein the particular heart sound of the particular heart sound waveform includes an ensemble averaged heart sound over multiple physiological cycles;
- wherein the recognizing the first intra heart sound energy indication and the corresponding first intra heart sound time indication within the particular heart sound includes recognizing within at least a portion of one of S1, S2, S3, and S4; and
- wherein the recognizing the first intra heart sound energy indication and the corresponding first intra heart sound time indication corresponds to the at least a portion of one of S1, S2, S3, and S4, respectively.

19. The method of claim 18, wherein the receiving the heart sound information includes receiving S2 information;
- wherein the recognizing the first intra heart sound energy indication and the corresponding first intra heart sound time indication within the particular heart sound of the particular heart sound waveform includes recognizing an intra S2 energy indication and a corresponding intra S2 time indication within an S2 of the particular heart sound waveform; and
- wherein the using the heart sound information from the particular heart sound waveform and the heart sound information from the at least one other heart sound waveform includes using the S2 information from the particular heart sound waveform and the S2 information from at least one other heart sound waveform.

20. The method of claim 18, wherein each physiological cycle of the multiple physiological cycles includes a cardiac cycle.

21. The method of claim 18, wherein the using the heart sound information from the at least one other heart sound waveform includes using the heart sound information from an immediately preceding heart sound waveform to the particular heart sound waveform.

22. The method of claim 18, wherein the recognizing the first intra heart sound energy indication and the corresponding first intra heart sound time indication includes using a heart sound template and comparing the heart sound information from the particular heart sound waveform to the heart sound template.

23. The method of claim 22, wherein the using the heart sound template includes updating the heart sound template using at least a portion of the heart sound information from the at least one other heart sound waveform.

24. The method of claim 22, wherein the recognizing the first intra heart sound energy indication and the corresponding first intra heart sound time indication includes cross correlating between at least a portion of the heart sound information from the particular heart sound waveform and at least a portion of the heart sound template.

25. The method of claim 18, including:
- implantably sensing a heart sound signal;
- implantably detecting at least one heart sound feature using the heart sound signal; and
- wherein the using the heart sound information includes using the at least one heart sound feature.

26. The method of claim 18, including:
- detecting at least one first candidate heart sound for the particular heart sound of the at least one other heart sound waveform using the heart sound information, wherein detecting the at least one first candidate heart sound includes detecting an intra heart sound energy indication and a corresponding intra heart sound time indication;
- detecting at least one second candidate heart sound for the particular heart sound of the particular heart sound waveform using the heart sound information, wherein detecting the at least one second candidate heart sound includes detecting an intra heart sound energy indication and a corresponding intra heart sound time indication; and
- wherein the recognizing the first intra heart sound energy indication and the corresponding first intra heart sound time indication includes using:
  - the at least one detected first candidate heart sound; and
  - the at least one detected second candidate heart sound.

27. The method of claim 26, wherein the recognizing the at least one first candidate heart sound for the particular heart sound of the at least one other heart sound waveform includes recognizing the at least one first candidate heart sound for the particular heart sound of an immediately preceding heart sound waveform to the particular heart sound waveform.

28. The method of claim 26, including calculating a cost for the at least one second candidate heart sound, including:
- calculating a jump penalty indicative of a temporal cost associated with the at least one second candidate heart sound; and
- calculating a local score indicative of a local benefit associated with the at least one second candidate heart sound; and
- wherein the recognizing the first intra heart sound energy indication and the corresponding first intra heart sound time indication includes using the calculated cost.

29. The method of claim 28, including calculating a back pointer that indicates a pointer from the at least one second candidate heart sound to an optimal at least one first candidate heart sound using the cost analysis.

30. The method of claim 18, including:
- disregarding the recognized first intra heart sound energy indication and the corresponding recognized first intra heart sound time indication using a comparison of:

the recognized first intra heart sound energy indication and the corresponding recognized first intra heart sound time indication; and at least one other recognized intra heart sound energy indication and a corresponding at least one other recognized intra heart sound time indication within the particular heart sound of at least one other heart sound waveform.

31. The method of claim 30, including:

recapturing the disregarded recognized first intra heart sound energy indication and the corresponding disregarded recognized first intra heart sound time indication using a comparison of:

the disregarded recognized first intra heart sound energy indication and the corresponding disregarded recognized first intra heart sound time indication; and at least one other recognized intra heart sound energy indication and a corresponding at least one other recognized intra heart sound time indication within the particular heart sound of at least one other heart sound waveform.

32. A non-transitory machine-readable medium containing instructions that, when executed by one or more processors, causes the one or more processors to:

receive heart sound information; recognize a first intra heart sound energy indication and a corresponding first intra heart sound time indication within a particular heart sound of a particular heart sound waveform using the heart sound information from the particular heart sound waveform and the heart sound information from at least one other heart sound waveform;

wherein the particular heart sound of the particular heart sound waveform includes an ensemble averaged heart sound over multiple physiological cycles;

wherein the first intra heart sound energy indication and the corresponding first intra heart sound time indication within the particular heart sound includes at least a portion of one of S1, S2, S3, and S4; and wherein the first intra heart sound energy indication and the corresponding first intra heart sound time indication correspond to the at least a portion of one of S1, S2, S3, and S4, respectively.

33. The non-transitory machine-readable medium of claim 32, wherein the machine readable medium contains instructions that, when executed by the one or more processors, causes the one or more processors to:

detect at least one first candidate heart sound for the particular heart sound of the at least one other heart sound waveform using the heart sound information, wherein detecting the at least one first candidate heart sound includes detecting an intra heart sound energy indication and a corresponding intra heart sound time indication;

detect at least one second candidate heart sound for the particular heart sound of the particular heart sound waveform using the heart sound information, wherein detecting the at least one second candidate heart sound includes detecting an intra heart sound energy indication and a corresponding intra heart sound time indication; and recognize the first intra heart sound energy indication and the corresponding first intra heart sound time indication using:

the at least one detected first candidate heart sound; and the at least one detected second candidate heart sound.

34. The non-transitory machine-readable medium of claim 33, wherein the machine readable medium contains instructions that, when executed by the one or more processors, causes the one or more processors to:

calculate a jump penalty indicative of a temporal cost associated with the at least one second candidate heart sound; and calculate a local score indicative of a local benefit associated with the at least one second candidate heart sound; and calculate a cost for the at least one second candidate heart sound using the jump penalty and the local score;

recognize the first intra heart sound energy indication and the corresponding first intra heart sound time indication includes using the calculated cost.

35. The non-transitory machine-readable medium of claim 32, wherein the machine readable medium contains instructions that, when executed by the one or more processors, causes the one or more processors to:

disregard the recognized first intra heart sound energy indication and the corresponding recognized first intra heart sound time indication using a comparison of:

the recognized first intra heart sound energy indication and the corresponding recognized first intra heart sound time indication; and at least one other recognized intra heart sound energy indication and a corresponding at least one other recognized intra heart sound time indication within the particular heart sound of at least one other heart sound waveform.

* * * * *